US009518086B2

(12) United States Patent
Sanghvi et al.

(10) Patent No.: US 9,518,086 B2
(45) Date of Patent: Dec. 13, 2016

(54) CRYSTALLINE AND AMORPHOUS FORMS OF A β-ARRESTIN EFFECTOR

(71) Applicant: Trevena, Inc., King of Prussia, PA (US)

(72) Inventors: Ritesh Sanghvi, East Northport, NY (US); Gregory Alcorn, Valley Forge, PA (US); Graham Richard Lawton, Smithtown, NY (US); Meiki Yu, Jamaica, NY (US); Matthew Ronsheim, Port Jefferson, NY (US); Jiaher Tian, Syosset, NY (US); Shao Hong Zhou, Commack, NY (US); Yuriy B. Kalyan, Staten Island, NY (US)

(73) Assignee: Trevena, Inc., King of Prussia, PA (US)

( * ) Notice: Subject to any disclaimer, the term of this patent is extended or adjusted under 35 U.S.C. 154(b) by 0 days.

(21) Appl. No.: 14/616,487

(22) Filed: Feb. 6, 2015

(65) Prior Publication Data

US 2015/0225461 A1    Aug. 13, 2015

Related U.S. Application Data

(60) Provisional application No. 61/936,914, filed on Feb. 7, 2014.

(51) Int. Cl.
*C07K 7/06* (2006.01)
*A61K 38/00* (2006.01)

(52) U.S. Cl.
CPC ......... *C07K 7/06* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 3,751,404 A | 8/1973 | Sipos et al. | |
| 3,932,624 A | 1/1976 | Fulton | |
| 3,960,830 A * | 6/1976 | Bayer | A61K 47/48215 525/54.11 |
| 4,115,538 A | 9/1978 | Satoh et al. | |
| 4,298,523 A | 11/1981 | Heavner | |
| 4,547,489 A | 10/1985 | Goldstein et al. | |
| 5,112,807 A | 5/1992 | Hamano et al. | |
| 5,182,264 A | 1/1993 | Watkins | |
| 5,436,128 A | 7/1995 | Harpold et al. | |
| 5,629,292 A | 5/1997 | Rodgers et al. | |
| 5,889,020 A | 3/1999 | Huxley et al. | |
| 5,958,884 A | 9/1999 | Kifor et al. | |
| 8,486,885 B2 * | 7/2013 | Yamashita | A61K 38/08 514/1.1 |
| 8,796,204 B2 | 8/2014 | Yamashita et al. | |
| 8,809,260 B2 | 8/2014 | Yamashita et al. | |
| 2003/0017970 A1 | 1/2003 | Rodgers et al. | |
| 2004/0214836 A1 | 10/2004 | Cheresh et al. | |
| 2005/0202029 A1 | 9/2005 | Zabel et al. | |
| 2007/0286863 A1 | 12/2007 | Sinal et al. | |
| 2009/0280113 A1 | 11/2009 | Graham et al. | |
| 2010/0092974 A1 | 4/2010 | Zabel et al. | |
| 2010/0150990 A1 | 6/2010 | Greaves et al. | |
| 2010/0184701 A1 | 7/2010 | Yamashita et al. | |

FOREIGN PATENT DOCUMENTS

| | | |
|---|---|---|
| EP | 498361 | 8/1992 |
| WO | 9003181 | 4/1990 |
| WO | 9203145 | 3/1992 |
| WO | 9213564 | 8/1992 |
| WO | 9614858 | 5/1996 |
| WO | 9963930 | 12/1999 |
| WO | 2008018792 | 2/2008 |
| WO | 2009137465 A2 | 11/2009 |
| WO | 2010077339 | 7/2010 |
| WO | 2011035332 | 3/2011 |
| WO | 2011163619 A1 | 12/2011 |
| WO | 2012150890 * | 11/2012 |
| WO | 2012150890 A1 | 11/2012 |

OTHER PUBLICATIONS

Spyroulias et al., Eur. J. Biochem., 2003, 270(10) 2163-73.*
Goldsmith et al., J. Am. Coll. Cardiol., 1993, 21(5), 1107-13.*
Carpino et al., J. Org. Chem., 1972, 37(22), 3404-3409.*
Non-final Office Action dated Aug. 27, 2015 in related U.S. Appl. No. 14/461,081.
Spyroulias et al., Comparison of the solution structures of angiotensin I & II: implication for structure-function relationship, Eur J Biochem 2003 270(10):2163-73.
Goldsmith et al., Angiotensin II and sympathetic activity in patients with congestive heart failure, J Am Coll Cardiol 1993 21(5):1107-13.
Fukamizu et al., Structure and expression of the human angiotensinogen gene: identification of a unique and highly active promoter, J Biol Chem 1990 265(13):7576-82.
Carpenter et al., The octapeptide angiotensin II adopts a well-defined structure in a phospholipid environment, Eur J Biochem 1998 251(1-2):448-53.
Lage et al., Angiotensin II contributes to arteria Icompliance in congestive heart failure, Am J Physiol Heat Circ Physiol 2002 283(4):H1424-29.
International Search Report and Written Opinion of the International Searching Authority dated May 21, 2015 for International Application No. PCT/US15/14892.
Vestergarrd-Bogind et al., "Single-file diffusion through the Ca2+-activated K+ channel of human red cells" J Membrane Bio (1985) 88(1):67-75.

(Continued)

Primary Examiner — James H Alstrum Acevedo
Assistant Examiner — Roy Teller
(74) Attorney, Agent, or Firm — Pepper Hamilton LLP

(57) ABSTRACT

The present disclosure provides novel crystalline forms of a compound that acts as a β-arrestin effector, processes for preparing novel crystalline and amorphous forms of a compound that acts as a β-arrestin effector and uses thereof.

25 Claims, 23 Drawing Sheets

(56) References Cited

OTHER PUBLICATIONS

Violin et al, Selectively engaging b-arrestins at the angiotensin II type 1 receptor reduces blood pressure and increases cardiac performance, The Journal of Pharmacology and Experimental Therapeutics, vol. 335 No. 3 pp. 572-579, 2012.
Violin, J. et al., "Beta-arrestin-biased ligands at seven-transmembrane receptors." Trends Pharmacal Sci., 2007, 28(8):416-422.
Vrecl et al., "Agonist-induced endocytosis and recycling of the gonadotropin-releasing hormone receptor: effect of beta-arrestin on internalization kinetics," Mol Endocrinol (1996) 12:1818-1829.
Wilkie et al., "Characterization of G-protein alpha subunits in the Gq class: expression in murine tissues and in stromal and hematopoietic cell lines," Proc Nat'l Acad Sci USA (1991) 88(22):1 0049-10053.
Wittamer et al., "Specific recruitment of antigen-presenting cells by chemerin, a novel processed ligand from human inflammatory fluids," Journal of Experimental Medicine (2003) 198(7):977-985.
Wittamer et al., "The C-terminal nonapeptide of mature chemerin activates the chemerin receptor with low nanomolar potency," Journal of Biological Chemistry (2004) 279(11):9956-9962.
Wollenberg et al., "Plasmacytoid dendritic cells: a new cutaneous dendritic cell subset with distinct role in inflammatory skin diseases," Journal of Investigative Dermatology (2002) 119(5): 1096-1102.
Zabel et al., "Chemokine-like receptor 1 expression and chemerin-directed chemotaxis distinguish plasmacytoid from myeloid dendritic cells in human blood," Journal of Immunology (2010) 174:244-251.
Zabel et al., "Chemokine-like receptor 1 expression by macrophages in vivo: regulation by TGF-beta and TLR ligands," Experimental Hematology (2006) 34(8): 1106-1114.
Jorgensen et al, Angiotensin II Analogs. Stereochemical Factors in the 5 Position Influencing Pressor Activity, Journal of Medicinal Chemistry, 1971, vol. 14, No. 10.
Notice of Allowance received in related U.S. Appl. No. 14/449,647.
Notice of Allowance received in related U.S. Appl. No. 12/647,810 dated Mar. 8, 2013.
Notice of Allowance received in related U.S. Appl. No. 13/925,170 dated Apr. 14, 2014.
Notice of Allowance received in related U.S. Appl. No. 13/926,766 dated Jun. 3, 2014.
Non-Final Office Action received in related U.S. Appl. No. 13/755,637 dated Oct. 15, 2013.
Notice of Allowance received in related U.S. Appl. No. 13/755,637.
Ackerman et al., "Ion channels—basic science and clinical disease," New Eng J Med (1997) 336(22):1575-1595.
Aumelas, A. et al., "Studies on Angiotensin II and Analogs: Impact of Substitution in Position 8 on Conformation and Activity", Proc. Natl. Acad. Sci., 1985, 82:1881-1885.
Barak et al., "Internal trafficking and surface mobility of a functionally intact beta2-adrenergic receptor—green fluorescent protein conjugate," Mol Pharmacal (1997) 51 (2):177-184.
Barnea et al., "The genetic design of signaling cascades to record receptor activation," PNAS (2008) 105(1):64-69.
Berridge et al., "Inositol trisphosphate, a novel second messenger in cellular signal transduction," Nature (1984) 312 (5992):315-321.
Bohnet al., "Mu-opioid receptor desensitization by beta-arrestin-2 determines morphine tolerance but not dependence," Nature (2000) 408(6813):720-723.
Bourne et al., "The GTPase superfamily: a conserved switch for diverse cell functions," Nature (1990) 348 (6297): 125-132.
Bourne et al., "The GTPase superfamily: conserved structure and molecular mechanism," Nature (1991) 349 (6305):117-127.
Cash et al., "Synthetic chemerin-derived peptides suppress inflammation through ChemR23," Journal of Experimental Medicine (2008) 2005(4):767-775.

Conway et al, "Quantitative analysis of agonist-dependent parathyroid hormone receptor trafficking in whole cells using a functional green fluorescent protein conjugate," J Cell Physiol (2001) 189(3):341-355.
Daniel et al., "Screening for potassium channel modulators by a high through-put 86-rubidium efflux assay in a 96-well microtiter plate," J Pharmacal Meth (1991) 25(3): 185-193.
Dell'Italia, L., "Translational success stories: angiotensin receptor 1 antagonists in heart failure", Circ Res., 2011, 109 (4): 437-452.
DeWire, S. et al., "Biased ligands for better cardiovascular drugs: dissecting G-protein-coupled receptor pharmacology", Circ Res., 2011, 109(2):205-216.
Ernst et al., "Chemerin: at the crossroads of inflammation and obesity," Cell (2010) pp. 1-8.
Fehrentz et al., "An efficient synthesis of optically active alpha-(t-Butoxycarbonylamino)-aldehydes from alpha-amino acids," Synthesis (1983) pp. 676-678.
Felley-Bosco et al., "Constitutive expression of inducible nitric oxide synthase in human bronchial epithelial cells induces c-fos and stimulates the cGMP pathway," Am J Resp Cell and Mol Bio (1994) 11 (2):159-164.
Gantz et al., "Molecular cloning of a novel receptio (CMKLR1) with homology to the chemotactic factor receptors," Cytogenet Cell Genet (1996) 74 (4):286-290.
Gonzales et al., "Improved indicators of cell membrane potential that use fluorescence resonance energy transfer," Chern Bioi (1997) 4(4):269-277.
Groarke et al., "Visualization of agonist-induced association and trafficking of green fluorescent protein-tagged forms o both beta-arrestin-1 and the thyrotropin-releasing hormone receptor-1 ," J Bio Chern (1999) 274(33):23263-23269.
Hamill et al., "Improved patch-clamp techniques for high-resolution current recording from cells and cell-free membrane patches," PFiugers Archiv (1981) 391(2):85-100.
Holevinsky et al., "ATP-sensitive K+ channel opener acts as a potent CI—channel inhibitor in vascular smooth muscle cells," J Membrane Biology (1994) 137(1):57-70.
Kenakin, T ., "Functional selectivity and biased receptor signaling", J Pharmacal Exp Ther., 2011, 336{2}:296-302.
Kroeger et al., "Constitutive and agonist-dependent homo-oligomerization of the thyrotropin-releasing hormone receptor. Detection in living cells using bioluminescence resonanace energy transfer," J. Biol Chem (2001) 276 (16):12736-12743.
Laungsay et al., "Mouse ChemR23 is expressed in dendritic cell subsets and macrophages, and mediates an anti-inflammatory activity of chemerin in a lung disease model," Journal of Immunology (2009) 183:6489-6499.
Meder et al., "Characterization of human circulating TIG2 as a ligand for the orphan receptor ChemR23," FEBS Letters (2003) 555(3):495-499.
Merrifield et al., "Solid Phase Peptide Synthesis. I. The Synthesis of a Tetrapeptide," J Am Chern Soc. (1963) 85 (14):2149.
Mistili et al., "Applications of the green fluorescent protein in cell biology and biotechnology", Nature Biotechnology (1997) 15(10):961-964.
Non-Final Office Action dated Dec. 2, 2013 received in co-pending U.S. Appl. No. 13/925,170.
Non-Final Office Action dated Jun. 7, 2012 received in related U.S. Appl. No. 12/647,810.
Non-Final Office Action dated Oct. 24, 2012 received in related U.S. Appl. No. 12/647,810.
Hallet al, Angiotensin analogs: The influence of sarcosine substituted in position 1, J Pharmacal Exp Ther. Jan. 1974;188(1):222-8.
Offermans et al., "G alpha 15 and G alpha 16 couple a wide variety of receptors to phospholipase C.," J Bioi Chern (1995) 270(25): 15175-15180.
Parlee et al., "Serum chemerin levels vary with time of day and are modified by obesity and tumor necrosis factor-{alpha}," Endocrinology (2010) 151 (6):2590-2602.
Parolini et al., "The role of chemerin in the colocalization of NK and dendritic cell subsets into inflames tissues," Blood (2007) 555(3):495-499.

(56) References Cited

OTHER PUBLICATIONS

Patel et al., "Beta-Arrestin-Mediated Signaling in the Heart", NIH Public Access, Author Manuscript, Circ J., (2008) 72 (11): 1725-1729.
Pitcher et al., "G protein-coupled receptor kinases," Annu Rev Biochem (1998) 67:653-692.
Rajagopal, S. et al., "Quantifying Ligand Bias at Seven-Transmembrane Receptors. Molecular Pharmacology", 2011, 80(3):367-377.
Rattan et al., "Protein synthesis, posttranslational modifications, and aging," Ann NY Acad Sci (1992) 663:48-62.
Samanen et al. "An investigation of angiotensin II agonist and antagonist analogs with 5,5-dimethylthiazolidine-4-carboxylic acid and other constrained amino acids", J. Medicinal Chemistry, 1991, 34, 3036-3043.
Samanen et al. "Potent angiotensin II antagonists with non-beta-branched amino acids in position 5", J. Medicinal Chemistry, 1989, 32, 466-472.
Samanen et al, Effects of d-amino acid substitution on antagonist activities of angiotensin II analogues, Journal of Medicinal Chemistry, 1998 31:510-516.
Sasaki et al., "Solid phase synthesis of peptides containing the CH2NH peptide bond isostere," Peptides (1987) 8 (1):119-121.
Schoelkens, B.A. et al., "1 ,8 Disubstituted analogues of [IIe<5>] and [Val<5>] angiotensin II: difference in potency and specificity of angiotensin II antagonistic activity", Hoppe-Seyler's Zeitschrift Fur Physiologische Chemie, 1976, 357:825-838.
Seitter et al., "Analysis for protein modifications and nonprotein cofactors.," Meth Enzymol (1990) 182:626-646.
Sell et al., "Chemerin is a novel adipocyte-derived factor inducing insulin resistance in primary human skeletal muscle cells," Diabetes (2009) 58(12):2731-2740.
Shimamura et al., "Identification of a stable chemerin analog with potent activity toward ChemR23," Peptides (2009) 30:1529-1538.
Siegal et al., "The nature of the principal type 1 interferon-producing cells in human blood," Science (1999) 284 (5421): 1835-1837.
Smith et al., Tritiated D-ala1-peptide T binding: A pharmacologic basis for the design of drugs which inhibit HIV receptor binding, Drug Development Res (1988) 15:371-379.
Sozzani et al., "Trafficking properties of plasmacytoid dendritic cells in health and disease," Trends in Immunology (2010) 31:270-277.
Traynor et al., "Modulation by mu-opioid agonists of guanosine-5'-0-(3-[35S]thio)triphosphate binding to membranes from human neuroblastoma SH-SY5Y cells," Mol Pharmacal (1995) 47(4):848-854.
Non-Final Office Action dated Jun. 20, 2016 in U.S. Appl. No. 14/631,461.
Gavras, Hospital Chronicles 2008 3(3):100-101.
Khosla, Journal of Medicinal Chemistry 1977 20(8).
"MHRA", Losartan Potassium, PL 19364/0012-14 2008.
"Pharmacology", downloaded online on Jun. 10. 2016 from https://cramberry.net/sets/35114-pharmacology.
Paul et al., Stereochemically constrained peptides. Theoretical and experimental studies on the conformations of peptides containing 1-aminocyclohexanecarboxylic acid, Journal of the American Chemcical Society 1986 108 (20):6363-6370.

* cited by examiner

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: MeGly
<220> FEATURE:
<221> NAME/KEY: MOD_RES
<222> LOCATION: (8)..(8)
<223> OTHER INFORMATION: D-Ala

<400> SEQUENCE: 1

Xaa Arg Val Tyr Ile His Pro Xaa
1               5
```

CRYSTALLINE AND AMORPHOUS FORMS OF A β-ARRESTIN EFFECTOR

CROSS-REFERENCE TO RELATED APPLICATIONS

This application claims priority to and the benefit of U.S. Provisional Application No. 61/936,914, filed Feb. 7, 2014, which is hereby incorporated by reference in its entirety.

FIELD

The present disclosure describes novel crystalline forms of a compound that acts as β-arrestin effector, processes for preparing and precipitating amorphous and crystalline forms of the compound, and uses thereof.

BACKGROUND

U.S. Pat. No. 8,486,885 discloses peptides that act as GPCR agonist of GPCR receptors (e.g., angiotensin II). GPCR agonist causes activation of a heterotrimeric "G protein". Such activation leads to second messenger/downstream signaling (e.g., via diacylglycerol, inositol-triphosphate, calcium, etc.) causing changes in physiological function (e.g., blood pressure and fluid homeostasis). One particular peptide disclosed in U.S. Pat. No. 8,486,885 is referred to therein as "SEQ ID NO. 27", which has the following amino acid sequence: $NH_2$-Sarcosine L-Arginine L-Valine L-Tyrosine L-Isoleucine L-Histidine L-Proline D-Alanine —OH referred to as $NH_2$-Sar Arg Val Tyr Ile His Pro D-Ala-OH.

SEQ ID NO. 27 referred to in U.S. Pat. No. 8,486,885 (hereinafter referred as SEQ.ID.NO.1) is an agonist of β-arrestin/GRK-mediated signal transduction via AT1 angiotensin receptor. The amino acid sequence, including, but not limited to, formula, variables, derivatives, of the peptide or peptide mimetic of SEQ ID NO. 1, the ability of the compound to effect G protein-mediated signaling or GPCR activity, or the absence of such signaling/activity, methods for preparation of SEQ.ID.NO.1, and other related peptides are disclosed in U.S. Pat. No. 8,486,885, the contents of which are incorporated herein by reference in their entirety.

There remains a need in the art for improved forms of SEQ.ID.NO.1 with improved properties. There also remains a need in the art for improved processes for preparing the peptide of SEQ.ID.NO.1.

SUMMARY

The present disclosure provides novel crystalline modifications of the peptide of SEQ.ID.NO.1, processes for preparing SEQ.ID.NO.1, and optionally isolating such forms.

Surprisingly, the peptide of SEQ ID NO. 1 can be crystallized and is superior in properties. Surprisingly, amorphous SEQ ID NO. 1 can be prepared, by precipitating SEQ.ID.NO.1. Crystalline forms of SEQ ID NO. 1 are distinguished from prior art by improved stability, processability and can also be used in for pharmaceutical formulations.

In some embodiments, crystalline forms of SEQ.ID. NO. 1 are provided. In some embodiments, the crystalline form is Form I of SEQ.ID. NO. 1 (hereinafter, Form 1).

In some embodiments, the Form I is characterized by an X-ray powder diffraction pattern comprising a peak at about 18.5±0.5 degrees 2θ.

In some embodiments, the Form I is characterized by an X-ray powder diffraction pattern comprising a peak at about 10.1±0.5 degrees 2θ.

In some embodiments, the Form I is characterized by an X-ray powder diffraction pattern comprising a peak at about 8.2±0.5 degrees 2θ.

In some embodiments, the Form I is characterized by an X-ray powder diffraction pattern comprising a peak at about 20.2±0.5 degrees 2θ.

In some embodiments, the Form I is characterized by an X-ray powder diffraction pattern comprising a peak at about 24.4±0.5 degrees 2θ.

In some embodiments, the Form I is characterized by an X-ray powder diffraction pattern comprising peaks at about 18.5, and at about 10.1±0.5 degrees 2θ.

In some embodiments, the Form I is characterized by an X-ray powder diffraction pattern comprising peaks at about 10.1, and at about 8.2±0.5 degrees 2θ.

In some embodiments, the Form I is characterized by an X-ray powder diffraction pattern comprising peaks at about 8.2, and at about 20.2±0.5 degrees 2θ.

In some embodiments, the Form I is characterized by an X-ray powder diffraction pattern comprising peaks at about 20.2, and at about 10.1±0.5 degrees 2θ.

In some embodiments, the Form I is characterized by an X-ray powder diffraction pattern comprising peaks at about 20.2, and at about 24.4±0.5 degrees 2θ.

In some embodiments, the Form I is characterized by an X-ray powder diffraction pattern comprising peaks at about 20.2, at about 10.1, and at about 24.4±0.5 degrees 2θ.

In some embodiments, the Form I is characterized by an X-ray powder diffraction pattern comprising peaks at about 8.2, at about 18.5, and at about 20.2±0.5 degrees 2θ.

In some embodiments, the Form I is characterized by an X-ray powder diffraction pattern comprising peaks at about 18.5, at about 10.1, at about 8.2, at about 20.2, and at about 24.4±0.5 degrees 2θ.

In some embodiments, the Form I is characterized by an X-ray powder diffraction pattern comprising one or more peaks as shown in FIG. 4.

In some embodiments, the Form I is characterized by an X-ray powder diffraction pattern comprising one or more d-spacing values at about 10.7, at about 8.7, at about 4.7, at about 4.1, and at about 3.6±0.5 degrees angstroms.

In some embodiments, a pharmaceutical composition comprising a crystalline form of SEQ.ID. NO. 1 is provided.

In some embodiments, a pharmaceutical composition comprising a crystalline Form I of SEQ.ID. NO. 1 is provided.

In some embodiments, the pharmaceutical composition comprises Form I, wherein Form I is a peptide or a peptide mimetic of SEQ.ID.NO. 1.

In some embodiments, the pharmaceutical composition comprises Form I, wherein the peptide or a peptide mimetic is cyclic.

In some embodiments, the pharmaceutical composition comprises Form I, wherein the peptide or a peptide mimetic is dimerized.

In some embodiments, the pharmaceutical composition comprises Form I, wherein the peptide or a peptide mimetic is trimerized.

In some embodiments, the pharmaceutical composition comprises Form I, further comprising an additional drug for the treatment of a cardiovascular or a cardio renal disorder.

In some embodiments, a process for preparing a crystalline form of SEQ.ID. NO. 1, comprising crystallizing SEQ.ID.NO. 1 to form Form I and optionally isolating the Form I of SEQ.ID. NO. 1 is provided.

In some embodiments, a process for preparing SEQ.ID. NO. 1, comprising precipitating SEQ.ID.NO. 1 and optionally isolating SEQ.ID. NO. 1 is provided.

In some embodiments, a pharmaceutical composition comprising SEQ.ID.NO.1 prepared by precipitating SEQ.ID.NO.1 is provided.

In some embodiments, a method of treating a cardiovascular or a cardiorenal disorder comprising administering to a patient in need thereof, a crystalline or an amorphous form of SEQ.ID. NO. 1 is provided.

In some embodiments, a method of treating a cardiovascular or a cardiorenal disorder comprising administering to a patient in need thereof, a crystalline Form I of SEQ.ID. NO. 1 is provided.

The details of one or more embodiments are set forth in the description below. Other features, objects, and advantages of the present teachings will be apparent from the description of examples and also from the appending claims.

DEFINITIONS

Figure 1:
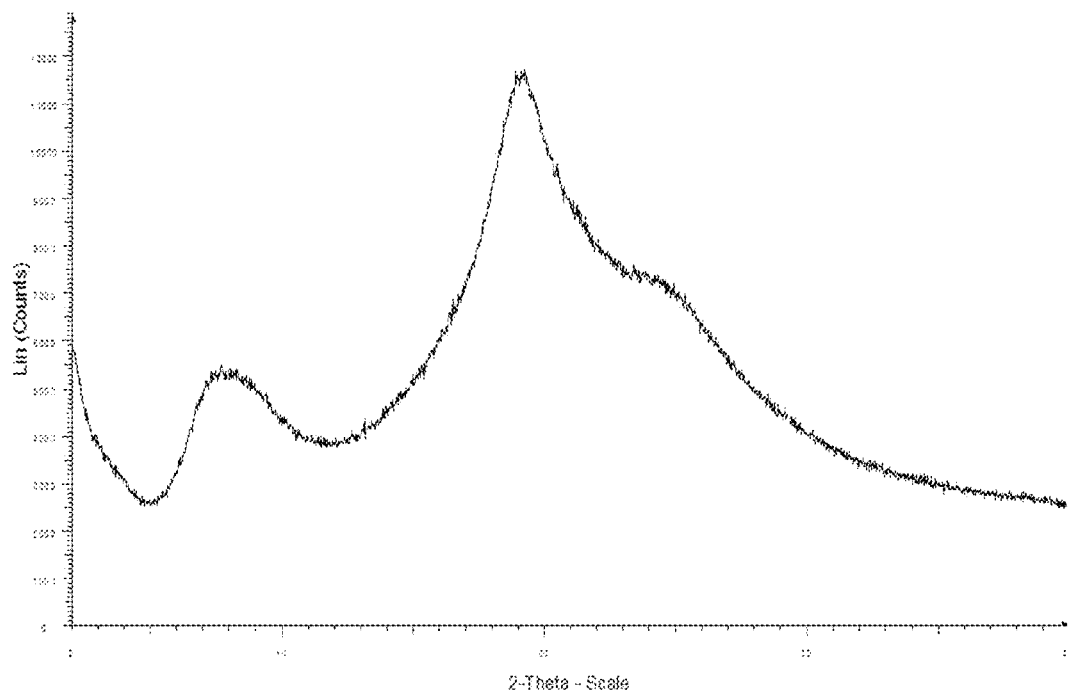
FIG. 1 shows X-ray powder diffraction pattern of amorphous SEQ ID. NO. 1.

The terms "peptidyl" and "peptidic" include active derivatives, variants, and/or mimetics of the peptides according to the present embodiments. Peptidic compounds are structurally similar bioactive equivalents of the peptides according to the present embodiments.

The term "structurally bioactive equivalent" means a peptidyl compound with structure sufficiently similar to that of an identified bioactive peptide to produce substantially equivalent therapeutic effects. For example, peptidic compounds derived from the amino acid sequence of the peptide, or having an amino acid sequence backbone of the peptide, are considered structurally similar bioactive equivalents attic peptide.

The term "variant" refers to a protein or polypeptide in which one or more amino acid substitutions, deletions, and/or insertions are present as compared to the amino acid sequence of a protein or peptide and include naturally occurring allelic variants or alternative splice variants of a protein or peptide.

The term "variant" includes the replacement of one or more amino acids in a peptide sequence with a similar or homologous amino acid(s) or a dissimilar amino acid(s). In some embodiments, variants include alanine substitutions at one or more of amino acid positions. Other preferred substitutions include conservative substitutions that have little or no effect on the overall net charge, polarity, or hydrophobicity of the protein.

The term "variant" also encompasses polypeptides that have the amino acid sequence of the proteins/peptides of the present compounds with at least one and up to 25 (e.g., 1, 2, 3, 4, 5, 6, 7, 8, 9, 10, 15, 20) additional amino acids flanking either the 3' or 5' end of the amino acid sequence or both. The term "variant" also refers to a protein that is at least 60 to 99 percent identical (e.g., 60, 65, 70, 75, 80, 85, 90, 95, 98, 99, or 100%, inclusive) in its amino acid sequence of the proteins of the present compounds as determined by standard methods that are commonly used to compare the similarity in position of the amino acids of two polypeptides. The degree of similarity or identity between two proteins can be readily calculated by known methods.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type proteins. Derivatives include salts. Such chemical modifications are well described in basic texts and in more detailed monographs, as well as in research literature and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, Proteins—Structure and Molecular Properties, $2^{nd}$ Ed., T. E. Creighton, W. H. Freeman and Company, New York (1993) and Wold, F., "Post-translational Protein Modifications: Perspectives and Prospects," pages. 1-12 in Posttranslational Covalent Modification Of Proteins, B. C. Johnson, Ed., Academic Press, New York (1983); Seifter et al., Meth. Enzymol. 182:626-646 (1990) and Rattan et al., "Protein Synthesis: Posttranslational Modifications and Aging," Ann N.Y. Acad. Sci. 663: 48-62 (1992).

The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). The term peptide mimetic is used in a broader sense to include molecules that are no longer completely peptidic in nature, such as pseudo-peptides, semi-peptides and peptoids. Whether completely or partially non-peptide, peptide mimetics according to the embodiments provide a spatial arrangement of reactive chemical moieties that closely resemble the three-dimensional arrangement of active groups in the peptide on which the peptide mimetic is based. As a result of this similar active-site geometry, the peptide mimetic has effects on biological systems that are similar to the biological activity of the peptide.

The peptide mimetics of the embodiments are preferably substantially in both three-dimensional shape and biological activity to the peptide described herein. According to some embodiments, peptide mimetics of the present compounds have protective groups at one or both ends of the compounds, and/or replacement of one or more peptide bonds with non-peptide bonds. Such modifications may render the compounds less susceptible to proteolytic cleavage than the compound itself. For instance, one or more peptide bonds can be replaced with an alternative type of covalent bond (e.g., a carbon-carbon bond or an acyl bond). Peptide mimetics can also incorporate amino-terminal or carboxyl terminal blocking groups such as t-butyloxycarbonyl, acetyl, alkyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl, thereby rendering the mimetic less susceptible to proteolysis. Non-peptide bonds and carboxyl- or amino-terminal blocking groups can be used singly or in combination to render the mimetic less susceptible to proteolysis than the corresponding peptide/compound. Additionally, substitution of D-amino acids for the normal L-stereoisomer can be effected, e.g., to increase the half-life of the molecule.

The term "salt" or "salts" may refer to any acid addition salts, including addition salts of free acids or addition salts of free bases. All of these salts (or other similar salts) may be prepared by conventional means. All such salts are acceptable provided that they are non-toxic and do not substantially interfere with the desired pharmacological activity.

The term "therapeutically effective amount" means the amount of a compound that, when administered to a mammal for treating a state, disorder or condition is sufficient to effect a treatment (as defined below). The "therapeutically effective amount" will vary depending on the compound, the disease and its severity, the age, weight, physical condition and responsiveness of the mammal to be treated.

The term "pharmaceutically acceptable" means biologically or pharmacologically compatible for in vivo use in animals or humans, and preferably means approved by a regulatory agency of the Federal or a State government or listed in the U.S. Pharmacopeia or other generally recognized pharmacopeia for use in animals, and more particularly in humans.

The term "treat", in all its verb forms, means to relieve or alleviate at least one symptom of a cardiovascular disorder or a cardiorenal disorder in a subject, including chronic hypertension, hypertensive crisis, acute congestive heart failure, angina, acute myocardial infarction, left ventricular failure, cerebrovascular insufficiency, intracranial haemorrhage, heart failure, acute decompensated heart failure, essential hypertension, post-operative hypertension, hypertensive heart disease, hypertensive renal disease, renovascular hypertension, malignant hypertension, post-renal transplant patient stabilization, dilated cardiomyopathy, myocarditis, post-cardiac transplant patient stabilization, disorders associated with post-stent management, neurogenic hypertension, pre-eclampsia, abdominal aortic aneurysm, and any cardiovascular disorder with a hemodynamic component. Specifically in some aspects, the cardiovascular disorder is an acute cardiovascular disorder. In other specific aspects, the acute cardiovascular disorder is acute hypertensive crisis, toxemia of pregnancy, acute myocardial infarction, acute congestive heart failure, acute ischaemic heart disease, pulmonary hypertension, post-operative hypertension, migraine, retinopathy and post-operative cardiac/valve surgery.

The term "synergy" is defined as the interaction of two or more agents so that their combined effect is greater than the sum of their individual effects. For example, if the effect of drug A alone in treating a disease is 25%, and the effect of drug B alone in treating a disease is 25%, but when the two drugs are combined the effect in treating the disease is 75%, the effect of A and B is synergistic.

The term "additive" is defined as the interaction of two or more agents so that their combined effect is the same as the sum of their individual effects. For example, if the effect of drug A alone in treating a disease is 25%, and the effect of drug B alone in treating a disease is 25%, but when the two drugs are combined the effect in treating the disease is 50%, the effect of A and B is additive.

The term "pharmaceutically acceptable" or "therapeutically acceptable" refers to molecular entities and compositions that are physiologically tolerable and preferably do not typically produce an allergic or similar untoward reaction, such as gastric upset, dizziness and the like, when administered to a human. Preferably, as used herein, the term "pharmaceutically acceptable" means approved by a regulatory agency of the Federal or a State government or listed in the U.S. Pharmacopeia or other generally recognized pharmacopeia (e.g., Remington's Pharmaceutical Sciences, Mack Publishing Co. (A. R. Gennaro edit. 1985)) for use in animals, and more particularly in humans.

The term "approximately" means plus or minus 5%.

Approximately 80% and 20% vv of ethanol and the remainder of the solution approximately is water means a solution comprising between approximately 80% v/v ethanol and 20% v/v water to approximately 20% v/v ethanol and 80% v/v water.

Approximately 80% and 20% v/v isopropyl alcohol and the remainder of the solution approximately is water means a solution comprising between approximately 80% v/v isopropyl alcohol and 20% vv water to approximately 20% v/v isopropyl alcohol and 80% v/v water.

Approximately 80% and 20% v/v of acetone and the remainder of the solution approximately is water means a solution comprising between approximately 80% v/v acetone and 20% v/v water to approximately 20% v/v acetone and 80% v/v water.

DETAILED DESCRIPTION

The present embodiments relate to a synthetic octapeptide, namely SEQ.ID.NO.1, having the amino sequence structure as follows: NH$_2$-Sar Arg Val Tyr Ile His Pro D-Ala-OH. SEQ. ID NO. 1 is an agonist of β-arrestin GRK-mediated signal transduction via the AT1 angiotensin receptor.

An amorphous form of SEQ ID. NO. 1 can be prepared using solid-phase peptide synthesis using FMOC based solid state synthesis on a chlortriyl resin. The crude peptide can be purified by reverse phase chromatography and ion-exchange can be performed to remove trifluroacetic acid and to replace it with acetic acid. The amorphous form of SEQ ID. NO. 1 can then be isolated using lyophilization. Lyophilization may not be feasible for a large scale manufacturing of the peptide for commercial production.

The present application relates to novel methods of precipitating SEQ. ID. NO. 1 and novel crystalline forms of SEQ. ID. NO. 1.

Figure 2:
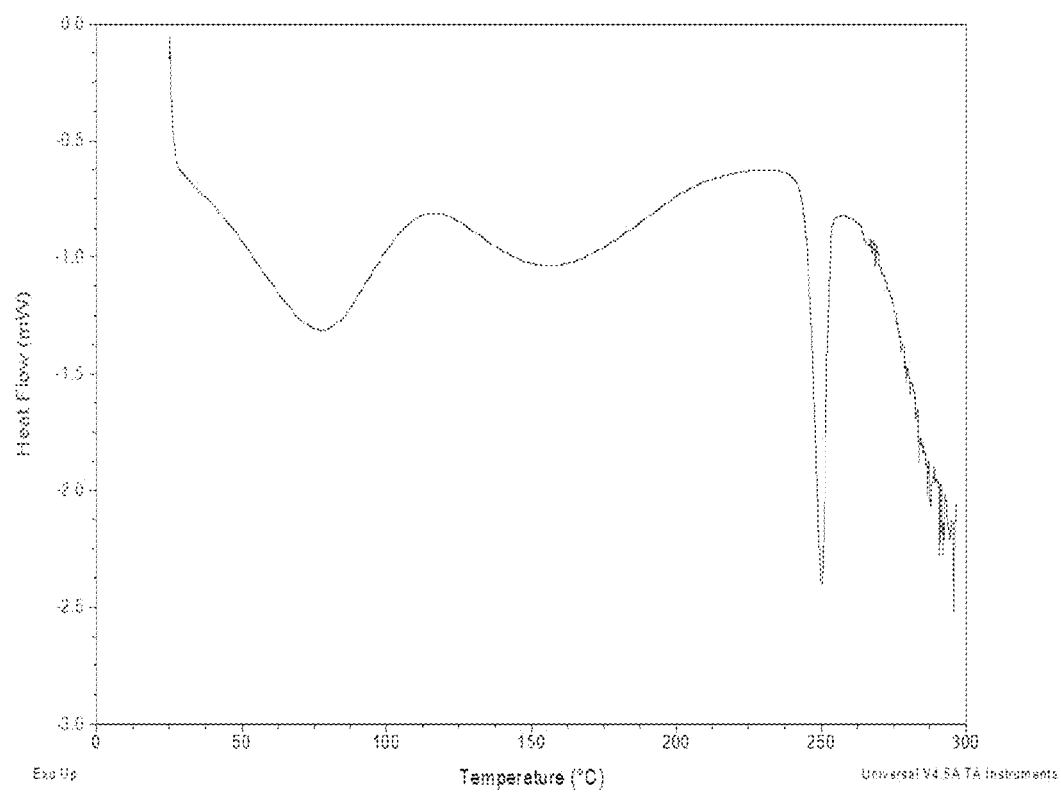
FIG. 2 shows Differential Scanning calorimetry (DSC) thermogram of amorphous SEQ. ID. NO. 1.
Figure 3:
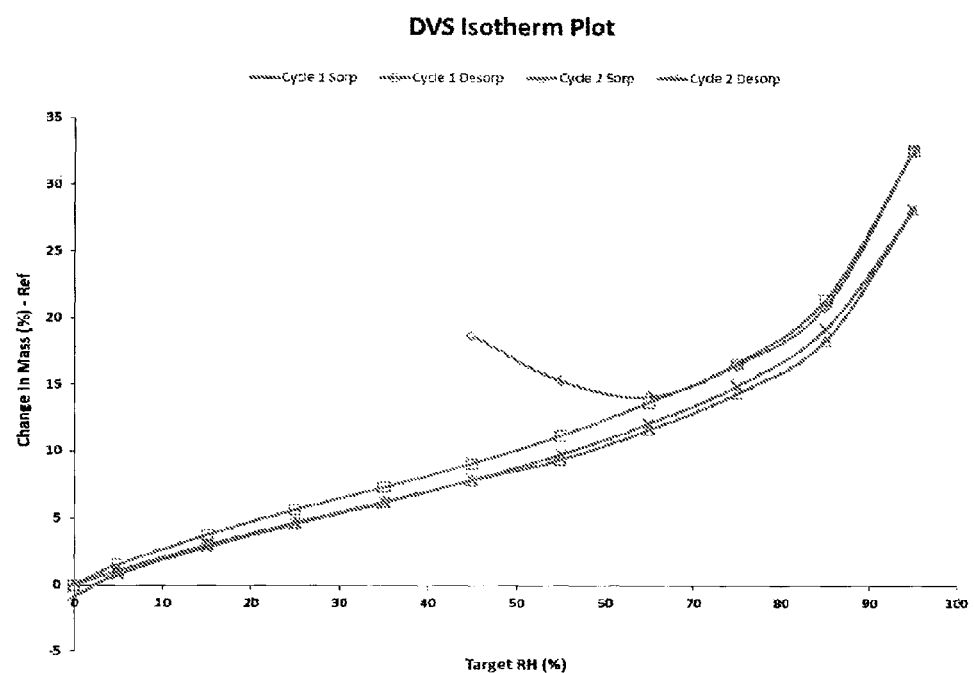
FIG. 3 shows Sorption/Desorption profile of amorphous SEQ ID. NO. 1.

An example of an amorphous form of SEQ. ID. NO. 1., is illustrated in FIG. 1, which shows a X-ray powder diffraction pattern of amorphous SEQ ID. NO. 1. FIG. 2 shows an example of a Differential Scanning calorimetry (DSC) thermogram of amorphous SEQ. ID. NO. 1. FIG. 3 shows an example of Sorption/Desorption profile of amorphous SEQ ID. NO. 1.

DSC thermogram shown in FIG. 2 exhibits two broad endotherm at around 76° C. and at around 159° C., as well as sharp endotherm at around 250° C. SEQ. ID. NO. 1 is highly hygroscopic as it adsorbed moisture with increase in % RH. More than about 25% (by weight) moisture was adsorbed at 95% RH at 25° C. as shown in FIG. 3. FIGS. 1-3 show that the peptide of SEQ. ID. NO. 1 is amorphous.

In some embodiments, crystalline forms of SEQ ID NO. 1 are provided. In some embodiments crystalline Form I of SEQ ID NO. 1 is provided.

Figure 4:
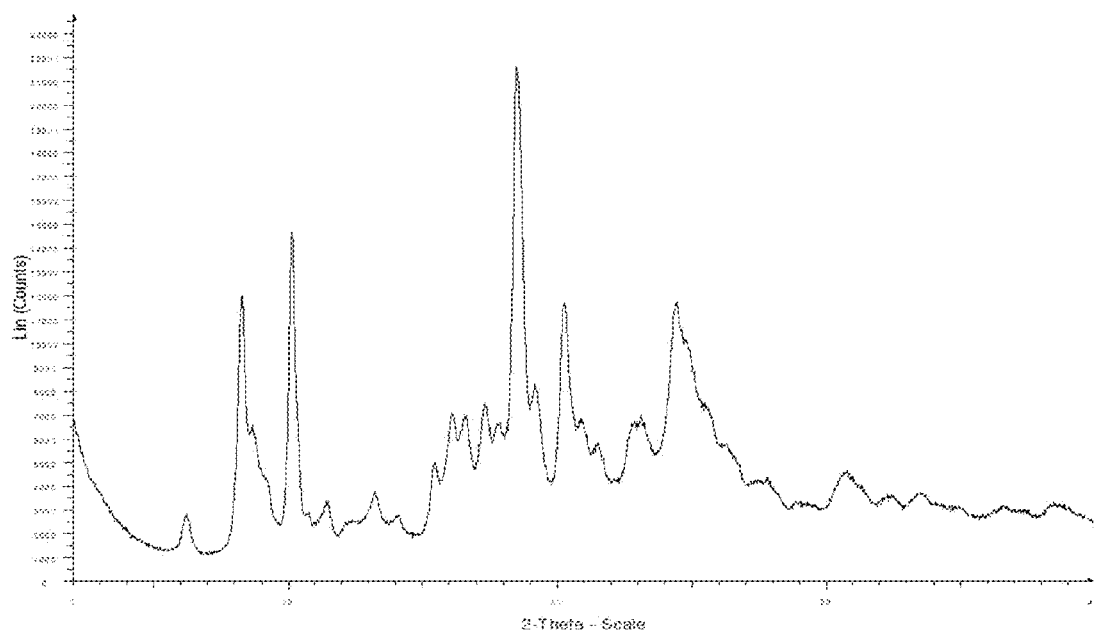
FIG. 4 shows X-ray powder diffraction pattern of crystalline Form I of SEQ ID. NO. 1.

In some embodiments, the Form I is characterized by an X-ray powder diffraction pattern substantially as shown in FIG. 4. In some embodiments, Form I is characterized by an X-ray powder diffraction pattern comprising one or more peaks as provided in Table 1. In some embodiments, Form I is characterized by an X-ray powder diffraction pattern comprising substantially all of, or all of, the peaks as provided in Table 1.

In some embodiments, the Form I is characterized by an X-ray powder diffraction pattern comprising a peak at about 8.2±0.5 degrees 2θ.

In some embodiments, the Form I is characterized by an X-ray powder diffraction pattern comprising a peak at about 10.1±0.5 degrees 2θ.

In some embodiments, the Form I is characterized by an X-ray powder diffraction pattern comprising a peak at about 15.4±0.5 degrees 2θ.

In some embodiments, the Form I is characterized by an X-ray powder diffraction pattern comprising a peak at about 16.5±0.5 degrees 2θ.

In some embodiments, the Form I is characterized by an X-ray powder diffraction pattern comprising a peak at about 18.5±0.5 degrees 2θ.

In some embodiments, the Form I is characterized by an X-ray powder diffraction pattern comprising a peak at about 20.2±0.5 degrees 2θ.

In some embodiments, the Form I is characterized by an X-ray powder diffraction pattern comprising a peak at about 23.1±0.5 degrees 2θ.

In some embodiments, the Form I is characterized by an X-ray powder diffraction pattern comprising a peak at about 24.4±0.5 degrees 2θ.

In some embodiments, the Form I is characterized by an X-ray powder diffraction pattern comprising a peak at about 30.8±0.5 degrees 2θ.

In some embodiments, the Form I is characterized by an X-ray powder diffraction pattern comprising peaks at about 8.2±0.5 degrees 2θ, about 10.1±0.5 degrees 2θ, about 18.5±0.5 degrees 2θ, about 20.2±0.5 degrees 2θ, about 24.4±0.5 degrees 2θ.

In some embodiments, the Form I is characterized by an X-ray powder diffraction pattern comprising peaks at about 6.1±0.5 degrees 2θ, about 8.2±0.5 degrees 2θ, about 10.1±0.5 degrees 2θ, about 11.4±0.5 degrees 2θ, about 13.2±0.5 degrees 2θ, about 16.1±0.5 degrees 2θ, about 18.5±0.5 degrees 2θ, about 20.2±0.5 degrees 2θ, about 23.1±0.5 degrees 2θ, about 24.4±0.5 degrees 2θ, and about 30.8±0.5 degrees 2θ.

In some embodiments, the Form I is characterized by an X-ray powder diffraction pattern comprising peaks at about 6.1±0.5 degrees 2θ, about 8.2±0.5 degrees 2θ, about 10.1±0.5 degrees 2θ, about 10.7±0.5 degrees 2θ, about 12.3±0.5 degrees 2θ, about 14.0±0.5 degrees 2θ, about 15.4±0.5 degrees 2θ, about 16.1±0.5 degrees 2θ, about 17.3±0.5 degrees 2θ, about 18.5±0.5 degrees 2θ, about 19.1±0.5 degrees 2θ, about 20.2±0.5 degrees 2θ, about 20.9±0.5 degrees 2θ, about 21.5±0.5 degrees 2θ, about 24.4±0.5 degrees 2θ, and about 30.8±0.5 degrees 2θ.

In some embodiments, the Form I is characterized by an X-ray powder diffraction pattern comprising peaks at about 8.2±0.5 degrees 2θ, and at about 10.1±0.5 degrees 2θ. In some embodiments, the Form I is characterized by an X-ray powder diffraction pattern comprising peaks at about 10.1±0.5 degrees 2θ and at about 18.5±0.5 degrees 2θ. In some embodiments, the Form I is characterized by an X-ray powder diffraction pattern comprising peaks at about 18.5±0.5 degrees 2θ and at about 20.2±0.5 degrees 2θ. In some embodiments, the Form I is characterized by an X-ray powder diffraction pattern comprising peaks at about 20.2±0.5 degrees 2θ and at about 24.4±0.5 degrees 2θ.

In some embodiments, the Form I is characterized by an X-ray powder diffraction pattern comprising peaks at about 8.2±0.5 degrees 2θ, at about 10.1±0.5 degrees 2θ and at about 18.5±0.5 degrees 2θ.

In some embodiments, the Form I is characterized by an X-ray powder diffraction pattern comprising peaks at about 18.5±0.5 degrees 2θ, at about 20.2±0.5 degrees 2θ and at about 24.4±0.5 degrees 2θ.

In some embodiments, the Form I is characterized by an X-ray powder diffraction pattern comprising peaks at about 8.2±0.5 degrees 2θ, at about 10.1±0.5 degrees 2θ, at about 18.5±0.5 degrees 2θ and at about 20.2±0.5 degrees 2θ.

In some embodiments, the Form I is characterized by an X-ray powder diffraction pattern comprising peaks at about 8.2±0.5 degrees 2θ, at about 10.1±0.5 degrees 2θ, at about 18.5±0.5 degrees 2θ, and optionally one or more peaks at about 16.5±0.5 degrees 2θ and/or about 23.1±0.5 degrees 2θ.

In some embodiments, the Form I is characterized by an X-ray powder diffraction pattern comprising peaks at about 8.2±0.5 degrees 2θ, about 10.1±0.5 degrees 2θ, about 18.5±0.5 degrees 2θ, about 20.2±0.5 degrees 2θ, about 24.4±0.5 degrees 2θ and optionally having one or more peaks at about at about 6.1±0.5 degrees 2θ, about 11.4±0.5 degrees 2θ, about 13.2±0.5 degrees 2θ, about 16.1±0.5 degrees 2θ, about 23.1±0.5 degrees 2θ, about 30.8±0.5 degrees 2θ.

In some embodiments, the Form I is characterized by an X-ray powder diffraction pattern comprising peaks at about 8.2±0.5 degrees 2θ, about 10.1±0.5 degrees 2θ, about 18.5±0.5 degrees 2θ, about 20.2±0.5 degrees 2θ, about 24.4±0.5 degrees 2θ and optionally having one or more peaks at about 6.1±0.5 degrees 2θ, about 10.7±0.5 degrees 2θ, about 12.3±0.5 degrees 2θ, about 14.0±0.5 degrees 2θ, about 15.4±0.5 degrees 2θ, about 16.1±0.5 degrees 2θ, about 17.3±0.5 degrees 2θ, about 19.1±0.5 degrees 2θ, about 20.2±0.5 degrees 2θ, about 20.9±0.5 degrees 2θ, about 21.5±0.5 degrees 2θ, about 30.8±0.5 degrees 2θ.

As used herein, unless otherwise indicated, the phrase "one or more peaks" should be understood to be inclusive of (i) crystalline forms that have XRD peaks at every peak value recited after this phrase, (ii) crystalline forms that have an XRD peak at only one of the peak values recited after this phrase, as well as (iii) crystalline forms that have XRD peaks at two or more (e.g., three or more, four or more, five or more, six or more, or even seven or more) of the peak values recited after this phrase.

Figure 5:
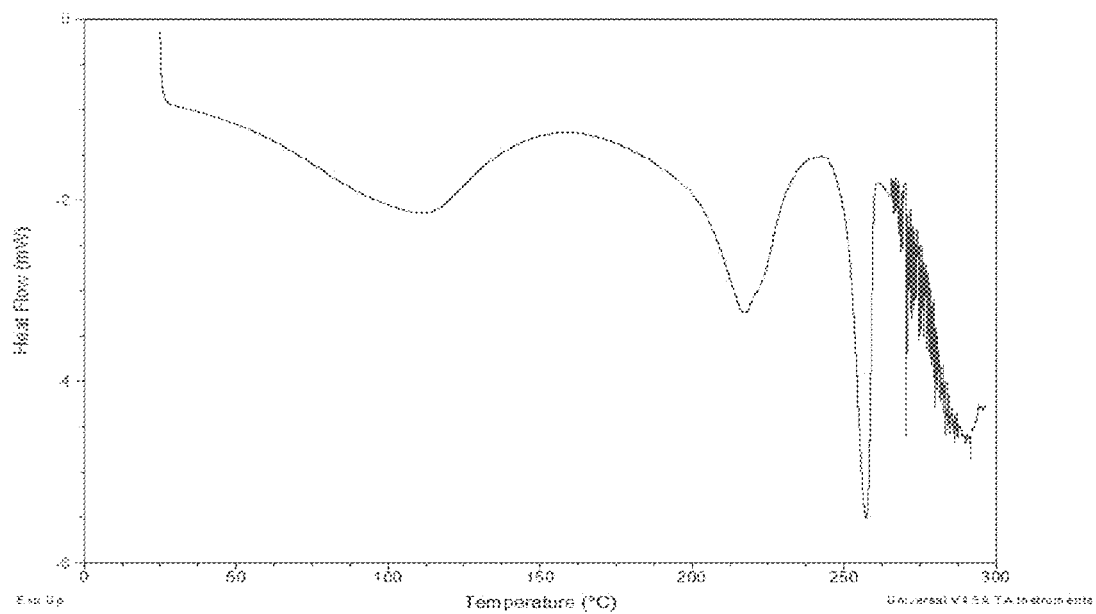
FIG. 5 shows Differential Scanning calorimetry (DSC) thermogram of crystalline Form 1 of SEQ. ID. NO. 1.

In some embodiments, the Form I is characterized by a DSC thermogram as shown in FIG. 5.

In some embodiments, the Form I is characterized by any combination of the above data.

In some embodiments, the X-ray powder fraction peaks recited herein for particular embodiments can vary by ±0.4 degrees 2θ, by ±0.3 degrees 2θ, by ±0.2 degrees 2θ, or by ±0.1 degrees 2θ.

In some embodiments, the Form I is characterized by an X-ray powder diffraction pattern comprising peaks having d-spacing values at about 10.7, at about 8.7, at about 4.7, at about 4.3, and at about 3.6±0.5 angstroms.

In some embodiments, the Form I is characterized by an X-ray powder diffraction pattern comprising a d-spacing value at about 10.7±0.5 angstroms.

In some embodiments, the Form I is characterized by an X-ray powder diffraction pattern comprising a d-spacing value at about 8.7±0.5 angstroms.

In some embodiments, the Form I is characterized by an X-ray powder diffraction pattern comprising a d-spacing value at about 5.7±0.5 angstroms.

In some embodiments, the Form I is characterized by an X-ray powder diffraction pattern comprising a d-spacing value at about 5.3±0.5 angstroms.

In some embodiments, the Form I is characterized by an X-ray powder diffraction pattern comprising a d-spacing value at about 4.7±0.5 angstroms.

In some embodiments, the Form I is characterized by an X-ray powder diffraction pattern comprising a d-spacing value at about 4.3±0.5 angstroms.

In some embodiments, the Form I is characterized by an X-ray powder diffraction pattern comprising a d-spacing value at about 3.8±0.5 angstroms.

In some embodiments, the Form I is characterized by an X-ray powder diffraction pattern comprising a d-spacing value at about 3.6±0.5 angstroms.

In some embodiments, the Form I is characterized by an X-ray powder diffraction pattern comprising a d-spacing value substantially as shown in Table 1.

In some embodiments, the X-ray powder diffraction peaks recited herein for particular embodiments having d-spacing values can vary by ±4% nm, by ±3% nm, by ±2% nm, or by ±1% nm or by ±4% angstroms, by ±3% angstroms, by ±2% angstroms, or by ±1% angstroms.

One skilled in the art will understand that the relative intensities and positions of the peaks obtained by X-ray powder diffraction may vary depending upon, inter alfa, the sample preparation technique, the sample mounting procedure, and the particular instrument employed. For example, in some embodiments, the listed X-ray powder diffraction pattern peaks for the crystalline Form I of SEQ ID. NO. 1 is about ±0.2 degrees 2θ.

Figure 6:
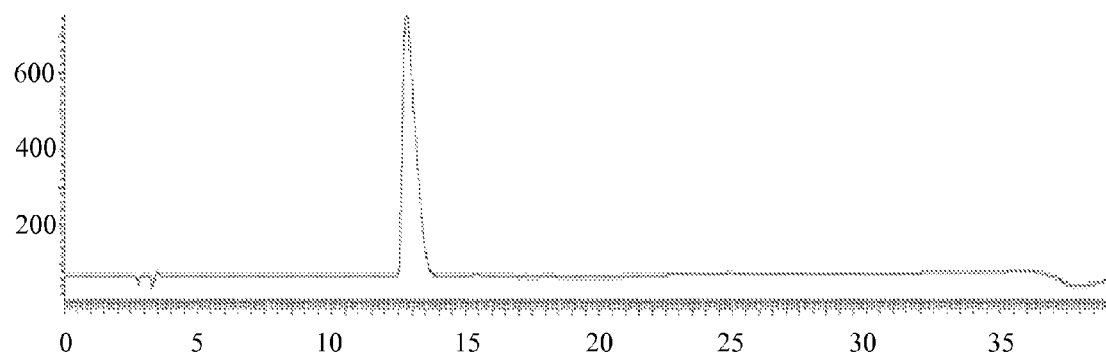
FIG. 6 shows HPLC chromatogram of Form I of SEQ ID. NO. 1.

In some embodiments, the crystalline Form I of SEQ. ID. NO. 1 is characterized using High Performance Liquid Chromatography and using microscopy. FIG. 6 shows an example of a HPLC chromatogram of Form I. Other methods for characterizing Form I could also be used.

Form I can have any desired degree of purity, relative to other substances or components in the preparation. In some embodiments, Form I is provided such that it is substantially pure, such as, for example, having greater than 30%, greater than 40%, greater than 50%, greater than 60%, greater than 70%, greater than 80%, greater than 85%, greater than 90%, greater than 95%, greater than 96%, greater than 97%, greater than 98%, greater than 99%, greater than 99.2%, greater than 99.4%, greater than 99.5%, greater than 99.6%, greater than 99.7%, or greater than 99.9% purity, relative to other substances or components in the preparation.

In exemplary embodiments, the. Form I is about 45% to 95% pure, such as, for example, about 50% to 95% pure, about 55% to 90% pure, about 60% to 95% pure, or about 70% to 99% pure, relative to other substances or components in the preparation. In some embodiments, the Form I is about 95% to 99% pure. In some embodiments, Form I is about 90% to 95% pure. In some embodiments, the Form I is about 85% to 90% pure. In some embodiments, the Form I is about 80% to 85% pure. In some embodiments, the Form I is about 75% to 80% pure. In some embodiments, the Form 1 is about 70% to 75% pure. In certain embodiments, the Form I is about 65% to 70% pure. In some embodiments, the Form I is about 60% to 65% pure. In other embodiments, the Form I is about 55% to 60% pure. In yet other embodiments, the Form I is about 50% to 55% pure. In some embodiments, Form I is about 45% to 50% pure.

In some embodiments, the Form I may comprise one or more impurities and/or a degradation product, such as a hydrolysis product, acetylation product, a formylation product, an oxidation product, a water-mediated degradation product, and/or a deamidation product. In some embodiments, a composition comprising Form I may comprise one or more impurities and/or a degradation product, such as a hydrolysis product, acetylation product, a formylation product, an oxidation product, a water-mediated degradation product, and/or deamidation product. In some embodiments, the one or more impurities may be biologically active.

In some embodiments, Form I and/or the composition comprising Form I can contain any desired purity relative to hydrolysis product(s). In some embodiments, the composition comprises less than about 10% by weight of hydrolysis product(s), relative to the total weight of Form I and/or the composition, such as, tier example, less than about 7.5 wt. %, less than about 5 wt. %, or less than about 2 wt. % of hydrolysis product(s). In some embodiments, Form I and/or the composition comprises from about 0.05% to about 5% by weight of hydrolysis product(s). In some embodiments, Form I and/or the composition comprises from about 0.05% to about 2% by weight of the hydrolysis product(s). In some embodiments, Form I and/or the composition comprises from about 0.1% to about 2% by weight of the hydrolysis product(s). In some embodiments, Form I and/or the composition comprises from about 0.01% to about 2% by weight of the hydrolysis product(s).

Alternatively, or in addition, Form I and/or the composition comprising Form I can contain any desired purity relative to acetylation product(s). In some embodiments, the acetylation product may comprise less than 10% by weight of the Form I and/or the composition. In some embodiments, the acetylation product may comprise less than 7.5% by weight of the Form 1 and/or the composition. In some embodiments, the acetylation product may comprise less than 5% by weight of the Form I and/or the composition. In some embodiments, the acetylation product may comprise less than 2% by weight of the Form I and/or the composition. In some embodiments, the acetylation product may comprise less than 1% by weight of the Form I and/or the composition. In some embodiments, the acetylation product may comprise less than 0.5% by weight of Form I and/or the composition. In some embodiments, the acetylation product may comprise from about 0.05% to about 5% by weight of Form I and/or the composition. In some embodiments, the acetylation product may comprise from about 0.05% to about 2% by weight of Form I and/or the composition. In some embodiments, the acetylation product may comprise from about 0.1% to about 2% by weight of Form I and/or the composition. In some embodiments, the acetylation product may comprise from about 0.01% to about 2% by weight of the composition.

Alternatively, or in addition, Form I and/or the composition comprising Form I can contain any desired purity relative to formylation product(s). In some embodiments, the formylation product may comprise less than 10% by weight of Form I and/or the composition. In some embodiments, the formylation product may comprise less than 7.5% by weight of Form I and/or the composition. In some embodiments, the formylation product may comprise less than 5% by weight of Form I and/or the composition. In some embodiments, the formylation product may comprise less than 2% by weight of Form I and/or the composition. In some embodiments, the formylation product may comprise from about 0.05% to about 5% by weight of Form I and/or the composition. In some embodiments, the formylation product may comprise from about 0.05% to about 2% by weight of Form I and/or the composition. In some embodiments, the formylation product may comprise from about 0.1% to about 2% by weight of Form I and/or the composition.

Alternatively, or in addition, Form I and/or the composition comprising Form I can contain any desired purity relative to oxidation product(s). In some embodiments, the oxidation product may comprise less than 10% by weight of Form I and/or the composition. In some embodiments, the oxidation product may comprise less than 7.5% by weight of Form I and/or the composition. In some embodiments, the oxidation product may comprise less than 5% by weight of Form I and/or the composition. In some embodiments, the oxidation product may comprise less than 2% by weight of Form I and/or the composition. In some embodiments, the oxidation product may comprise from about 0.05% to about 5% by weight of Form I and/or the composition. In some embodiments, the oxidation product may comprise from about 0.05% to about 2% by weight of Form I and/or the composition. In some embodiments, the oxidation product may comprise from about 0.1% to about 2% by weight of Form I and/or the composition. In some embodiments, the oxidation product may comprise from about 0.01% to about 2% by weight of Form I and/or the composition.

Alternatively, or in addition, Form I and/or the composition comprising Form I can contain any desired purity relative to water-mediated degradation product(s). In some embodiments, the water-mediated degradation product(s) may comprise less than 10% by weight of Form I and/or the composition. In some embodiments, the water-mediated degradation product(s) may comprise less than 7.5% by weight of Form I and/or the composition. In some embodiments, the water-mediated degradation product(s) may comprise less than 5% by weight of Form I and/or the composition. In other embodiments, the water-mediated degradation product(s) may comprise less than 2% by weight of Form I and/or the composition. In some embodiments, the water-mediated degradation product(s) may comprise from about 0.05% to about 5% by weight of Form I and/or the composition. In exemplary embodiments, the water-mediated degradation product(s) may comprise from about 0.05% to about 2% by weight of Form I and/or the composition. In some embodiments, the water-mediated degradation product(s) may comprise from about 0.1% to about 2% by weight of Form I and/or the composition. In some embodiments, the water-mediated degradation product(s) may comprise from about 0.01% to about 2% by weight of Form I and/or the composition Alternatively, or in addition, Form I and/or the composition comprising Form I can contain any desired purity relative to deamidation product(s). In some embodiments, the deamidation product may comprise less than 10% by weight of Form I and/or the composition. In some embodiments, the deamidation product may comprise less than 7.5% by weight of Form I and/or the composition. In some embodiments, the deamidation product may comprise less than 5% by weight of Form I and/or the composition. In other embodiments, the deamidation product may comprise less than 2% by weight of Form I and/or the composition. In some embodiments, the deamidation product may comprise from about 0.05% to about 5% by weight of Form I and/or the composition. In some embodiments, the deamidation product may comprise from about 0.05% to about 2% by weight of Form I and/or the composition. In some embodiments, the deamidation product may comprise from about 0.1% to about 2% by weight of Form I and/or the composition. In some embodiments, the deamidation product may comprise from about 0.01% to about 2% by weight of Form I and/or the composition.

In some embodiments, a composition is provided comprising Form I and less than 10 wt. % such as less than 8 wt. %, less than 6 wt. %, less than 5 wt. %, less than 4 wt. %, less than 3 wt. %, less than 2 wt. %, less than 1 wt. %, less than 0.5 wt. %, or less than 0.25 wt. % of a combined total of a degradation product, such as a hydrolysis product, a formylation product, an oxidation product, a water-mediated degradation product, and/or a deamidation product.

In some embodiments, a composition is provided comprising Form I and less than 20 wt. % such as less than 18 wt. %, less than 16 wt. %, less than 14 wt. %, less than 12 wt. %, less than 10 wt. %, less than 8 wt. %, less than 6 wt. %, less than 5 wt. %, less than 4 wt. %, less than 3 wt. %, less than 2 wt. %, less than 1 wt. %, less than 0.5 wt. %, or less than 0.25 wt. % of a combined total of a degradation product, such as a hydrolysis product, an acetylation product, a formylation product, an oxidation product, a water-mediated degradation product, and/or a deamidation product.

In some embodiments, a composition is provided comprising Form I and less than 10 wt. % such as less than 8 wt. %, less than 6 wt. %, less than 5 wt. %, less than 4 wt. %, less than 3 wt. %, less than 2 wt. %, less than 1 wt. %, less than 0.5 wt. %, or less than 0.25 wt. % of a combined total of one or more impurities and/or a degradation product, such as a hydrolysis product, a formylation product, an oxidation product, a water-mediated degradation product, and/or a deamidation product.

In some embodiments, a composition is provided comprising Form I and less than 20 wt. % such as less than 18 wt. %, less than 16 wt. %, less than 14 wt. %, less than 12 wt. %, less than 10 wt. %, less than 8 wt. %, less than 6 wt. %, less than 5 wt. %, less than 4 wt. %, less than 3 wt. %, less than 2 wt. %, less than 1 wt. %, less than 0.5 wt. %, or less than 0.25 wt. % of a combined total of one or more impurities and/or a degradation product, such as a hydrolysis product, an acetylation product, a formylation product, an oxidation product, a water-mediated degradation product, and/or a deamidation product.

In some embodiments, a composition is provided comprising Form I and multimers. In some embodiments, the multimers may be formed due to disulfide linkages. In some embodiments, the multimers may be formed due to non-disulfide linkages. In some embodiments, the composition may contain any desired purity relative to multimers. In some embodiments, the composition comprises less than about 20 wt. % of multimers, such as, for example, less than about 18 wt. %, less than about 16 wt. %, less than about 14 wt. %, less than about 12 wt. %, less than about 10 wt. %, less than about 8 wt. %, less than about 6 wt. %, less than about 5 wt. %, less than about 4 wt. %, less than about 3 wt. %, less than about 2 wt. %, less than about 1 wt. %, less than about 0.5 wt. %, or less than about 0.1 wt. % of multimers.

In some embodiments, a composition is provided comprising Form I and/or one more peptide mimetic of SEQ ID. NO. 1. In some embodiments, the composition may contain any desired purity relative to peptide mimetic of SEQ ID, NO. 1. For example, the composition may comprise less than about 20 wt. % of peptide mimetic, such as, for example, less than about 18 wt. %, less than about 16 wt. %, less than about 14 wt. %, less than about 12 wt. %, less than about 10 wt. %, less than about 8 wt. %, less than about 6 wt. %, less than about 5 wt. %, less than about 4 wt. %, less than about 3 wt. %, less than about 2 wt. %, less than about 1 wt. %, less than about 0.5 wt. %, or less than about 0.1 wt. % of peptide mimetic. In some embodiments, the peptide mimetic is cyclic. In some embodiments, the peptide mimetic is a dimer. In some embodiments, the peptide mimetic is a trimer.

In some embodiments, the compositions may comprise Form I and a dimer. In some embodiments, the composition comprises less than about 20 wt. % of dimers, such as, for example, less than about 18 wt. %, less than about 16 wt. %, less than about 14 wt. %, less than about 12 wt. %, less than about 10 wt. %, less than about 8 wt. %, less than about 6 wt. %, less than about 5 wt. %, less than about 4 wt. %, less than about 3 wt. %, less than about 2 wt. %, less than about 1 wt. %, less than about 0.5 wt. %, or less than about 0.1 wt. % of dimers.

In some embodiments, the compositions may comprise Form I and a trimer. In some embodiments, the composition comprises less than about 20 wt. % of trimers, such as, for example, less than about 18 wt. %, less than about 16 wt. %, less than about 14 wt. %, less than about 12 wt. %, less than about 10 wt. %, less than about 8 wt. %, less than about 6 wt. %, less than about 5 wt. %, less than about 4 wt. %, less than about 3 wt. %, less than about 2 wt. %, less than about 1 wt. %, less than about 0.5 wt. %, or less than about 0.1 wt. % of trimers.

In some embodiments, a composition is provided comprising Form I and an isomer. In some embodiments, the composition comprises less than about 20 wt. % of isomers, such as, for example, less than about 18 wt. %, less than about 16 wt. %, less than about 14 wt. %, less than about 12 wt. %, less than about 10 wt. %, less than about 8 wt. %, less than about 6 wt. %, less than about 5 wt. %, less than about 4 wt. %, less than about 3 wt. %, less than about 2 wt. %, less than about 1 wt. %, less than about 0.5 wt. %, or less than about 0.1 wt. % of isomers.

In some embodiments, a composition provided comprising Form I and less than about 40 wt %, such as less than about 30 wt. %, less than about 20 wt. %, less than about 15 wt. %, less than about 10 wt. %, less than about 8 wt. %, less than about 6 wt. %, less than about 5 wt. %, less than about 4 wt. %, less than about 3 wt. %, less than about 2 wt. %, less than about 1 wt. %, less than about 0.5 wt. %, less than about 0.1 wt. %, or less than about 0.01 wt. % of amorphous SEQ.ID. NO. 1.

In some embodiments, a composition is provided comprising from about 50:50 and 99:1 Form I to amorphous SEQ. ID. NO. 1, such as, for example, from about 55:45 and 95:5 Form I to amorphous SEQ. ID. NO. 1, from about 60:40 and 90:10 Form I to amorphous SEQ. ID. NO. 1, from about 70:30 and 85:15 Form I to amorphous SEQ. ID. NO. 1, or from about 75:25 and 99:1 Form I to amorphous SEQ. ID. NO. 1.

In some embodiments, processes for preparing crystalline forms of SEQ ID. NO. 1 are provided. In some embodiments, the crystalline Form I is produced by precipitating and crystallizing SEQ ID. NO. 1 and optionally isolating the Form I. In some embodiments, the Form I is prepared by precipitating and crystallizing SEQ ID. NO. 1 in an aqueous solution and optionally isolating the Form I. In some embodiments, the Form I is prepared by precipitating and crystallizing SEQ ID. NO. 1 in a super saturated aqueous solution and optionally isolating the Form I.

Any suitable aqueous solution can be used in this regard, such as, for example, water, DMSO, acids, and polar solvents, at various strengths or concentrations. Such solutions may include, but are not limited to, DMSO, water, ethanol, butanol, methanol, dicholoromethane, tetrahydofuran, ethyl acetate, acetone, dimethylformamide, acetonitrile, dimethyl sulfoxide, propylene carbonate, formic acid, isopropanol, propanol, acetic acid, and nitromethane. In some embodiments, the aqueous solution is selected from water, ethanol, propanol, dimethyl sulfoxide, acetone, and isopropanol. In some embodiments, the water does not have any additional components or solvents added to it. In some embodiments, the aqueous solution comprises water and acetone. In some embodiments, the aqueous solution comprises water and isopropyl alcohol. In some embodiments, the aqueous solution does not contain ethanol. In some embodiments, the aqueous solution does not contain acetone. In some embodiments, the aqueous solution does not contain organic solvents.

The crystalline Form I of SEQ ID NO. 1 may be identified, characterized, and distinguished from amorphous form using any suitable manner. One skilled in the art will know many different methods of identification and characterization of Form I of SEQ ID NO. 1. For example, the crystalline Form I of SEQ ID NO. 1 may be identified and characterized based on differences in diffraction, thermal, intensity, and/or spectroscopic properties of the amorphous and crystalline form. Suitable methods include, but are not limited to, X-ray diffractometry, capillary melting point determination, thermogravimetric analysis (TGA), differential scanning calorimetry (DSC), and/or spectroscopic methods.

In some embodiments, Form I is precipitated from water. FIGS. 4 and 5 shows an example characterization of Form I using X-ray powder diffraction and DSC. In some embodiments, Form I was precipitated from water and was characterized by HPLC and microscopy. FIG. 6 shows an example HPLC chromatogram of Form I.

Figure 7:
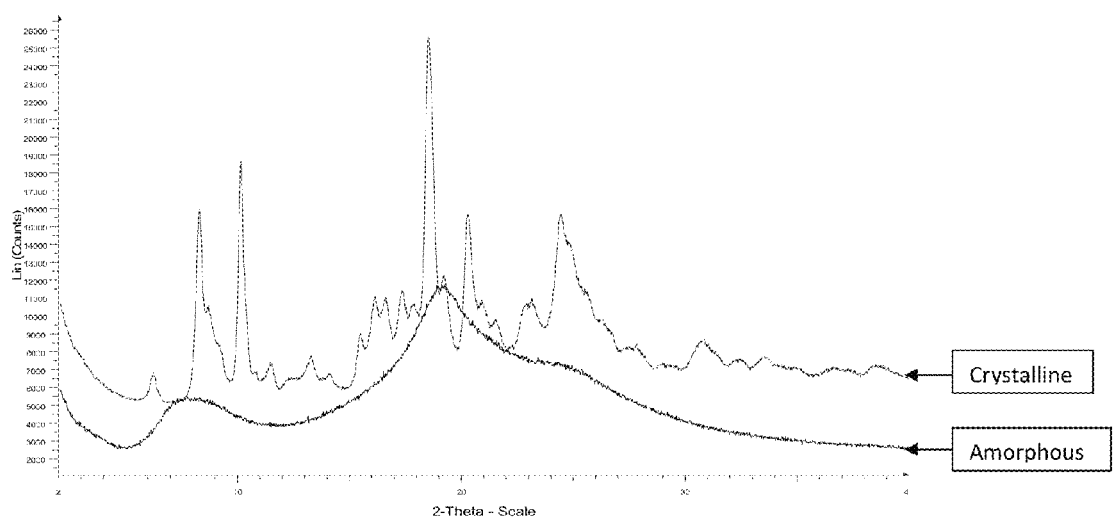
FIG. 7 shows overlaid X-ray powder diffraction patterns of amorphous SEQ ID. NO. 1 and crystalline Form I of SEQ ID. NO. 1.

FIG. 7 shows overlaid X-ray powder diffraction patterns of amorphous SEQ ID. NO. 1 and crystalline Form I of SEQ ID. NO. 1 obtained using aqueous solution. In some embodiments, Form I is precipitated from supersaturated aqueous solution. XRD characterization from supersaturated aqueous solution indicates that Form I is crystalline material as shown in FIG. 7. DSC thermogram of Form I in FIG. 5 also showed different endothermic transitions from the amorphous SEQ. ID. NO. 1, with the last endothermic peak appeared at around 255° C.-259° C.

Figure 8:
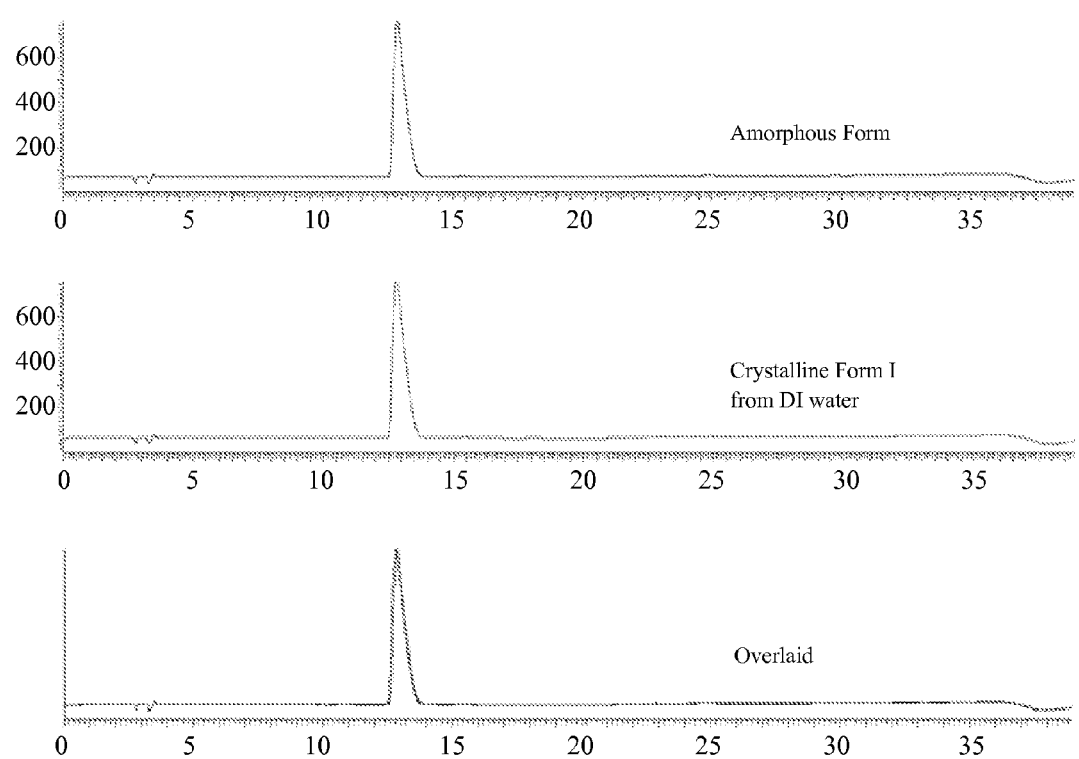
FIG. 8 shows HPLC chromatograms of amorphous and crystalline Form I of SEQ ID. NO. 1.

FIG. 8 shows exemplary HPLC chromatograms of amorphous and crystalline Form I of SEQ ID. NO. 1. The HPLC chromatograms shown in FIG. 8 confirmed that the crystalline form prepared from aqueous solution is chemically the same as SEQ. ID. NO. 1 amorphous form. These results demonstrate that Form I is a crystalline form of SEQ.ID. NO. 1.

Figure 9:
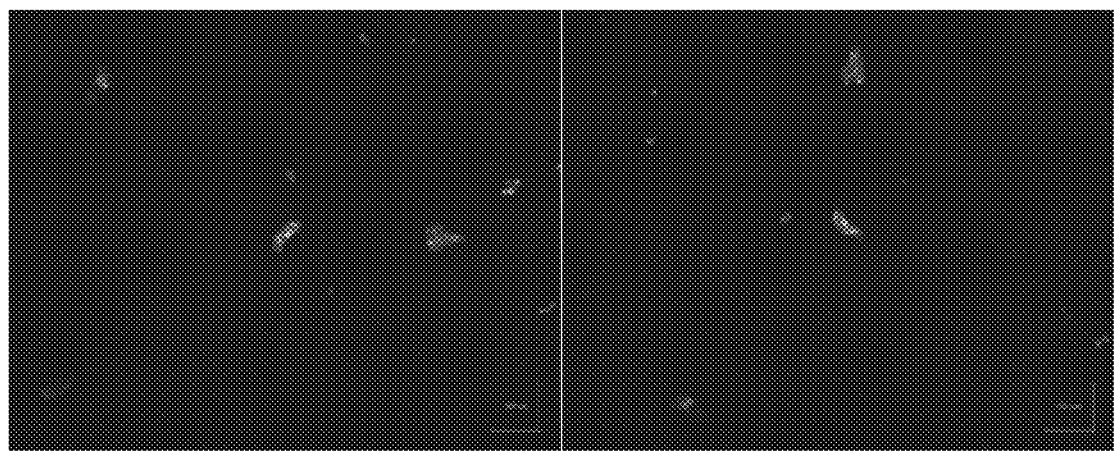
FIG. 9 shows microscopic image of crystalline Form I of SEQ ID. NO. 1 under cross polarized light.
Figure 10:
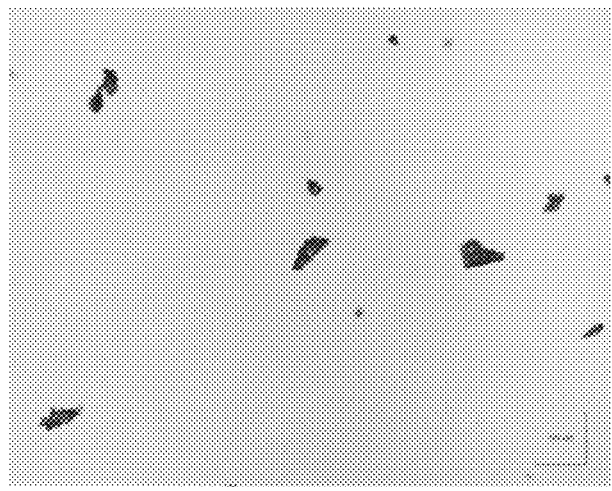
FIG. 10 shows microscopic image and particle size of crystalline Form I of SEQ ID. NO. 1 under plane polarized light.

Form I was further examined using polarized microscopy. FIG. 9 shows an example microscopic image of crystalline Form I under cross polarized light. FIG. 10 shows an example microscopic image and particle size of crystalline Form I under plane polarized light. These results confirmed that Form I was crystalline material as birefringence was observed in the sample under cross polarized light after turning the sample stage from 0° to 90° angle as shown in FIG. 9. The particle size was also determined as shown in FIG. 10 and Table 2.

In some embodiments, process for preparing the SEQ ID. NO. 1 are provided. In some embodiments, amorphous SEQ.ID.NO.1 is prepared by precipitating SEQ ID. NO. 1 and optionally isolating SEQ.ID.NO.1. In some embodiments, amorphous SEQ.ID.NO.1 was precipitated from a solution comprising ethanol. In some embodiments, amorphous SEQ.ID.NO.1 was precipitated from a solution comprising acetone. In some embodiments, amorphous SEQ.ID.NO.1 was precipitated from a solution comprising isopropyl alcohol.

In some embodiments, SEQ.ID.NO.1 can be dissolved in an aqueous solution of for example, without limiting, ethanol, wherein the percentage of ethanol in the solution may be from approximately 80% and 20% v/v and the remainder of the solution approximately is water. In some embodiments, the percentage of ethanol in the solution may be approximately 60% v/v and the remainder of the solution approximately is water. In some embodiments, the percentage of ethanol in the solution may be approximately 50% v/v and the remainder of the solution approximately is water. In some embodiments, the percentage of ethanol in the solution may be approximately 55% v/v and the remainder of the solution approximately is water. In some embodiments, the percentage of ethanol in the solution may be approximately 40% vv and the remainder of the solution approximately is water.

In some embodiments, SEQ.ID.NO.1 can be dissolved in an aqueous solution of, for example, without limiting, isopropyl alcohol, wherein the percentage of isopropyl alcohol in the solution may be from approximately 80% and 30% v/v and the remainder of the solution approximately is water. In some embodiments, the percentage of isopropyl alcohol in the solution may be approximately 60% v/v and the remainder of the solution approximately is water. In some embodiments, the percentage of isopropyl alcohol in the solution may be approximately 50% v/v and the remainder of the solution approximately is water. In some embodiments, the percentage of isopropyl alcohol in the solution may be approximately 55% v/v and the remainder of the solution approximately is water. In some embodiments, the percentage of isopropyl alcohol in the solution may be approximately 40% v/v and the remainder of the solution approximately is water.

In some embodiments, SEQ.ID.NO.1 can be dissolved in an aqueous solution of, for example, without limiting, acetone, wherein the percentage of acetone in the solution may be from approximately 80% and 20% v/v and the remainder of the solution approximately is water. In some embodiments, the percentage of acetone in the solution may be approximately 60% v/v and the remainder of the solution approximately is water. In some embodiments, the percentage of acetone in the solution may be approximately 50% v/v and the remainder of the solution approximately is water. In some embodiments, the percentage of acetone in the solution may be approximately 55% v/v and the remainder of the solution approximately is water. In some embodiments, the percentage of acetone in the solution may be approximately 40% v/v and the remainder of the solution approximately is water.

Additionally, any suitable aqueous solution can be used in this regard, such as, for example, water, DMSO, acids, and polar solvents, at various strengths or concentrations, Such solutions may include, but are not limited to, DMSO, water, ethanol, butanol, methanol, dicholoromethane, tetrahydrofuran, ethyl acetate, acetone, dimethylformamide, acetonitrile, dimethyl sulfoxide, propylene carbonate, formic acid, isopropanol, propanol, acetic acid, and nitromethane. In some embodiments, the solvent is selected from water, ethanol, propanol, dimethyl sulfoxide, acetone, and isopropanol.

Precipitates from, for example, but not limited to, the solutions described herein, including, but not limited to, ethanol, acetone/water and isopropyl alcohol/water produce precipitate showing the same XRD pattern as the amorphous SEQ.ID. NO. 1. The results described herein demonstrate that the precipitates contain amorphous, mostly amorphous, a mixture of amorphous and crystalline forms, one or more crystalline forms, or a mixture of amorphous and one or more crystalline forms. Each of the preceding are considered as separate embodiments.

In some embodiments, the precipitate of SEQ.ID. NO.1 from, for example, but not limited to, ethanol, acetone or isopropyl alcohol may comprise amorphous, mostly amorphous, a mixture of amorphous and crystalline forms, one or more crystalline forms, or a mixture of amorphous and one or more crystalline forms. Each of which are considered as a separate embodiments.

In some embodiments, a precipitate comprising between about 50:50 and 99:1 Form I to amorphous SEQ. ID. NO. 1 is provided. In some embodiments, the precipitate may comprise amorphous SEQ.ID.NO.1. In some embodiments, for example, the precipitate may comprise mostly amorphous SEQ.ID.NO.1 at about 99% to about 1% by weight, ranging from about less than 90%, less than 80%, less than 70%, less than 60%, less than 40%, less than 30%, less than 20%, less than 10%, less than 5%, less than 1%, less than 0.50%, less than 0.25% by weight.

In some embodiments, the precipitate may comprise mostly crystalline SEQ.ID.NO.1 at about 99% to about 1% by weight, ranging from about less than 90%, less than 80%, less than 70%, less than 60%, less than 40%, less than 30%, less than 20%, less than 10%, less than 5%, less than 1%, less than 0.50%, less than 0.25% by weight. In some other embodiments, for example, the precipitate may comprise one or more crystalline forms of SEQ.ID. NO. 1.

In some embodiments, the precipitate may comprise a mixture of one or more crystalline forms of SEQ.ID. NO. 1 and amorphous SEQ.ID.NO.1. For example, the precipitate may comprise crystalline SEQ.ID.NO.1 at about 99% to about 1% by weight, ranging from about less than 90%, less than 80%, less than 70%, less than 60%, less than 40%, less than 30%, less than 20%, less than 10%, less than 5%, less than 1%, less than 0.50%, or less than 0.25% by weight of the mixture. Alternatively, the precipitate may comprise amorphous SEQ.ID.NO.1 at about 99% to about 1% by weight, ranging from about less than 90%, less than 80%, less than 70%, less than 60%, less than 40%, less than 30%, less than 20%, less than 10%, less than 5%, less than 1%, less than 0.50%, or less than 0.25% by weight of the mixture.

The methods of precipitating can also comprise heating the solution comprising SEQ.ID.NO.1 and then allowing the solution to cool to ambient temperature. In some embodiments, ambient temperature is 20-25° C. In some embodiments, the solution is cooled to 10-20° C. In some embodiments, the solution is heated to at least, or about, 10, 20, 30, 40, 50, or 60° C. before being cooled or allowed to cool to ambient temperature or a specific temperature. In some embodiments, the solution is heated to about 10-20, 10-30, 10-40, 10-50, 20-30, 20-40, 20-50, 20-60, 30-40, 30-50, 30-60, 40-50, 40-60, 50-60, 25-45, 35-45, or 35-50, 45-55, or 45-60° C. In some embodiments, the solution is heated at given temperature for about 0.5 to about 2 hours, about 1 to about 2 hours, about 0.5 to about 1.5 hours, or about 1 to about 1.5 hours.

In some embodiments, the crystal form is precipitated at a temperature of about 15 to about 25° C., about 15 to about 23° C., about 15 to about 20° C., about 15 to about 18° C., about 17 to about 25° C., about 17 to about 23° C., about 17 to about 21° C., about 17 to about 20° C., about 18 to about 25° C., about 18 to about 23° C., about 18 to about 21° C., about 18 to about 20° C., about 19 to about 25° C., about 19 to about 23° C., or about 19 to about 21° C., or any temperature between the respective ranges. In some embodiments, the precipitates are allowed to form for about, or at least, 1, 2, 3, 4, 5, 6, 7, 8, 9, 10, 12, 18, or 24 hours. In some embodiments, the precipitates are allowed to form for about 2 to about 24, about 2 to about 18, about 2 to about 12, about 2 to about 10, about 2 to about 8, about 2 to about 6, about 2 to about 4, about 4 to about 24, about 4 to about 18, about 2 to about 12, about 4 to about 10, about 4 to about 8, about 4 to about 6, about 5 to about 24, about 5 to about 18, about 5 to about 12, about 5 to about 10, about 5 to about 8, about 5 to about 6, about 6 to about 24, about 6 to about 18, about 6 to about 12, about 6 to about 10, about 6 to about 8, about 8 to about 24, about 8 to about 18, about 8 to about 12, or about 8 to about 10 hours.

In some embodiments, an additional volume of water is added once the solution is heated and before it is cooled to the ambient or near ambient temperatures. In some embodiments, the solution is further cooled to about, or less than, 15, 10, 5, 0, −5, or −10° C. In some embodiments, the solution is cooled to about −5° C. to about 15° C., about −5° C. to about 10° C. about −5° C. to about 5° C., about −10° C. to about 15° C., about −10° C. to about 10° C., about −10° C. to about 5° C., about −10° C. to about 0° C., about −10° C. to about −5° C., about −5° C. to about 15° C., about −5° C. to about 10° C., about −5° C. to about 5° C., about −5° C. to about 0° C., about 0° C. to about 15° C. about 0° C. to about 10° C., about 0° C. to about 5° C., about 5° C. to about 15° C., or about 5° C. to about 10° C. In some embodiments, the solution is cooled for about, or at least, 1, 2, 3, 4, 5, 6, 12, 18, or 24 hours.

In some embodiments, the process comprises drying the precipitate. In some embodiments, the precipitate is dried under vacuum. In some embodiments, the precipitate is dried at a temperature of about 30° C. to about 50° C., about 35° C. to about 50° C., about 30° C. to about 45° C., about 35° C. to about 45° C., or about 40° C. to about 45° C. In some embodiments, the precipitate is dried at a temperature of about 30° C., about 35° C., about 40° C., or about 45° C., to about 50° C. For the avoidance of doubt, the drying can at a specific temperature can be performed under vacuum. In some embodiments, the dried material is also lyophilized.

In some embodiments, the precipitations steps described above can be repeated. In some embodiments, the process is repeated one, two, or three times.

Pharmaceutical Compositions/Formulations

Embodiments described herein can be used in pharmaceutical compositions and can be formulated by standard techniques using one or more physiologically acceptable carriers or excipients. In some embodiments, the formulations may contain a buffer and/or a preservative. Form I and their physiologically acceptable salts, anhydrates, hydrates and/or solvates, can be formulated for administration by any suitable route, including via inhalation, topically, nasally, orally, parenterally (for example, intravenously, intraperitoneally, intravesically or intrathecally) or rectally in a vehicle comprising one or more pharmaceutically acceptable carriers, the proportion of which is determined by the route of administration and standard biological practice. Other routes of administration are also described herein and can be used as well.

In some embodiments, pharmaceutical compositions are provided comprising effective amounts of Form I with, for example, pharmaceutically acceptable diluents, preservatives, solubilizers, emulsifiers, adjuvants and/or other carriers. Such compositions are known to one skilled in the art and the compositions can be formulated using standard techniques. For example, diluents of various buffer content such as, but not limited to, TRIS or other amines, carbonates, phosphates, amino acids, for example, glycinamide hydrochloride (especially in the physiological pH range), N-glycylglycine, sodium or potassium phosphate (dibasic, tribasic), etc. or TRIS-HCl or acetate), pH and ionic strength; additives such as detergents and solubilizing agents (e.g., surfactants such as Pluronics, Tween 20, Tween 80 (Polysorbate 80), Cremophor, polyols such as polyethylene glycol, propylene glycol, etc.), anti-oxidants (e.g., ascorbic acid, sodium metabisulfite), preservatives (e.g., Thimersol, benzyl alcohol, parabens, etc.) and bulking substances (e.g., sugars such as sucrose, lactose, mannitol, polymers such as polyvinylpyrrolidones or dextran, etc.); and/or incorporation of the material into particulate preparations of polymeric compounds such as polylactic acid, polyglycolic acid, etc. or into liposomes may be used. Hyaluronic acid may also be used. Such compositions can be employed to influence the physical state, stability, rate of in vivo release, and rate of in vivo clearance of a composition comprising Form I as described herein. See, e.g., Remington's Pharmaceutical Sciences, 18th Ed. (1990, Mack Publishing Co., Easton, Pa. 18042) pages 1.435-1712 which are herein incorporated by reference. Where a buffer is to be included in the formulations, the buffer can be, for example, but not limited to, sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, or mixtures thereof. Each buffer can be used independently or in combination with another buffer. In some embodiments, the buffer is glycylglycine, sodium dihydrogen phosphate, disodium hydrogen phosphate, sodium phosphate or mixtures thereof.

Where a pharmaceutically acceptable preservative is to be included in the formulations, the preservative can be, but is not limited to, phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. In some embodiments the preservative is phenol and/or m-cresol.

In some embodiments the preservative is present in a concentration from about 0.1 mg/ml to about 100 mg/ml, more preferably in a concentration from about 0.1 mg/ml to about 50 mg/ml, about 0.1 mg/ml to about 25 mg/ml. In some embodiments, the preservative is present in a concentration from about 0.1 mg/ml to about 10 mg/ml.

The use of a preservative in pharmaceutical compositions is well-known to the skilled person. For convenience reference is made to Remington: The Science and Practice of Pharmacy, 19th edition, 1995.

In some embodiments, the formulation may further comprise a chelating agent where the chelating agent may be salts of ethlenediaminetetraacetic acid (EDTA), citric acid, and aspartic acid, and mixtures thereof.

In some embodiments, the chelating agent is present in a concentration from 0.1 mg/ml to 10 mg/ml, particularly in a concentration from 0.1 mg/ml to 5 mg/ml. In some embodiments, the chelating agent is present in a concentration from 0.1 mg/ml to 2 mg/ml. In some embodiments, the chelating agent is present in a concentration from 2 mg/ml to 5 mg/ml.

The use of a chelating agent in pharmaceutical compositions is well-known to the skilled person. For convenience reference is made to Remington: The Science and Practice of Pharmacy, 19th edition, 1995.

In some embodiments, the formulation may further comprise a stabilizer selected from the group of high molecular weight polymers or low molecular compounds where such stabilizers include, but are not limited to, polyethylene glycol (e.g., PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine and mixtures thereof. In some embodiments, the stabilizer is L-histidine, imidazole, arginine, or any combination thereof.

In some embodiments, the high molecular weight polymer is present in a concentration from 0.1 mg/ml to 100 mg/ml, in a concentration from 01 mg/ml to 50 mg/ml. In some embodiments, the high molecular weight polymer is present in a concentration from 0.1 mg/ml to 5 mg/ml. In some embodiments, the high molecular weight polymer is present in a concentration from 5 mg/ml to 10 mg/ml. In some embodiments, the high molecular weight polymer is present in a concentration from 10 mg/ml to 20 mg/ml. In some embodiments, the high molecular weight polymer is present in a concentration from 20 mg/ml to 30 mg/ml. In some embodiments, the high molecular weight polymer is present in a concentration from 30 mg/ml to 50 mg/ml.

In some embodiments, the low molecular weight polymer is present in a concentration from 0.1 mg/ml to 100 mg/ml. In some embodiments, the low molecular weight polymer is present in a concentration from 0.1 mg/ml to 50 mg/ml. In some embodiments, the low molecular weight polymer is present in a concentration from 0.1 mg/ml to 5 mg/ml. In some embodiments, the low molecular weight polymer compound is present in a concentration from 5 mg/ml to 10 mg/ml. In some embodiments, the low molecular weight polymer is present in a concentration from 10 mg/ml to 2.0 mg/ml. In some embodiments, the low molecular weight polymer is present in a concentration from 20 mg/ml to 30 mg/ml. In some embodiments, the low molecular weight polymer is present in a concentration from 30 mg/ml to 50 mg/ml. In some embodiments, the low molecular weight polymer is present in a concentration from 50 mg/ml to 60 mg/ml. In some embodiments, the low molecular weight polymer is present in a concentration from 60 mg/m to 80 mg/ml. In some embodiments, the low molecular weight polymer is present in a concentration from 80 mg/ml to 100 mg/ml.

The use of a stabilizer in pharmaceutical compositions is well-known to the skilled person. For convenience reference is made to Remington: The Science and Practice of Pharmacy, 19th edition, 1995.

In some embodiments, the formulation may comprise a surfactant where a surfactant can be a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g., Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, docusate calcium, docusate potassium, SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g., 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g., lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, zwitterionic surfactants (e.g., N-alkyl-N,N-dimethylammonio-1-propanesulforiates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g., cetyl-trimethylammonium bromide, cetylpyridinium chloride), non-ionic surfactants,polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g., sodium tauro-dihydrofusidate etc.), long-chain fatty acids and salts thereof C6-C12 (e.g., oleic acid and caprylic acid), acylcarnitines and derivatives, $N_\alpha$-acylated derivatives of lysine, arginine or histidine, or side-chain acylated derivatives of lysine or arginine, $N_\alpha$-acylated derivatives of dipeptides comprising any combination of lysine, arginine or histidine and a neutral or acidic amino acid, $N_\alpha$-acylated derivative of a tripeptide comprising any combination of a neutral amino acid and two charged amino acids, imidazoline derivatives, or any mixture thereof.

The use of a surfactant in pharmaceutical compositions is well-known to the skilled person. For convenience reference is made to Remington: The Science and Practice of Pharmacy, 19th edition, 1995.

The formulations may also comprise a pharmaceutically acceptable sweetener. In some embodiments, the sweetener comprises at least one intense sweetener such as, but not limited to, saccharin, sodium or calcium saccharin, aspartame, acesulfame potassium, sodium cyclamate, alitame, a dihydrochalcone sweetener, monellin, stevioside sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, or from about 0.06% in the low-dosage formulations and about 0.08% in the high-dosage ones. The bulk sweetener can effectively be used in larger quantities ranging from about 10% to about 35% or from about 10% to 15% (w/v).

The formulations may be prepared by conventional techniques, for example, as described in Remington's Pharmaceutical Sciences, 1985 or in Remington: The Science and Practice of Pharmacy, 19th edition, 1995, where such conventional techniques of the pharmaceutical industry involve dissolving and mixing the ingredients as appropriate to give the desired end product.

Administration of the compound or the formulations described herein may be carried out using any method known in the art. For example, administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, inhalation, or by oral administration. In some embodiments, the compound or formulation is administered intravenously or by injection.

For oral administration, Form I or a therapeutically acceptable salt thereof can be formulated in unit dosage forms such as gelcaps, caplets, granules, lozenges, bulk powders, capsules or tablets. The tablets or capsules may be prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art.

Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For topical administration, Form I can be formulated in a pharmaceutically acceptable vehicle containing 0.1 to 10 percent, preferably 0.5 to 5 percent, of the active compound(s). Such formulations can be in the form of a cream, lotion, sublingual tablet, aerosols and/or emulsions and can be included in a transdermal or buccal patch of the matrix or reservoir type as are conventional in the art for this purpose.

For parenteral administration, Form I or an amorphous form of the compound can be administered by either intravenous, subcutaneous, or intramuscular injection, in compositions with pharmaceutically acceptable vehicles or carriers, Form I can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Additionally, the compound can be precipitated and stored in an ampule or other container and then dissolved in a solution prior to being administered to a subject.

For administration by injection, the compound can be used in solution, and, for example, in a sterile aqueous vehicle which may also contain other solutes such as buffers or preservatives as well as sufficient quantities of pharmaceutically acceptable salts or of glucose to make the solution isotonic. In some embodiments, the pharmaceutical compositions may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized. Suitable pharmaceutical carriers are described in "Remington's pharmaceutical Sciences" by E. W. Martin.

For administration by inhalation, the compound may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch. For intranasal administration the compound may be used, for example, as a liquid spray, as a powder or in the form of drops.

The compound can also be formulated in rectal compositions, for example, suppositories or retention enemas, for example, containing conventional suppository bases, for example, cocoa butter or other glycerides.

Furthermore, the compound can be formulated as a depot preparation. Such long-acting formulations can be administered by implantation (for example, subcutaneously or intramuscularly) or by intramuscular injection. Thus, for example, the compound can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack can also contain individual vials or other containers. The pack or dispenser device can be accompanied by instructions for administration.

Dosages

Crystalline Form I may be administered to a patient at therapeutically effective doses to prevent, treat, or control diseases and disorders mediated, in whole or in part, by a GPCR-ligand interaction described herein. Pharmaceutical compositions comprising crystalline Form I may be administered to a patient in an amount sufficient to elicit an effective protective or therapeutic response in the patient. The dose will be determined by the efficacy of the particular compound employed and the condition of the subject, as well as the body weight or surface area of the area to be treated. The size of the dose also will be determined by the existence, nature, and extent of any adverse effects that accompany the administration of a particular compound or vector in a particular subject.

The amount and frequency of administration of the compound comprising Form I or another amorphous form prepared according to a method described herein and/or the pharmaceutically acceptable salts thereof can be regulated according to the judgment of the attending clinician considering such factors as age, condition and size of the patient as well as severity of the symptoms being treated. An ordinarily skilled physician or veterinarian can readily determine and prescribe the effective amount of the drug required to prevent, counter or arrest the progress of the condition. In general it is contemplated that an effective amount would be from 0.001 mg/kg to 10 mg/kg body weight, and in particular from 0.01 mg/kg to 1 mg/kg body weight. More specifically it is contemplated that an effective amount would be to continuously infuse by intravenous administration from 0.01 micrograms/kg body weight/min to 100 micrograms/kg body weight/min for a period of 12 hours to 1.4 days. It may be appropriate to administer the required dose as two, three, four or more sub-doses at appropriate intervals throughout the day. Sub-doses may be formulated as unit dosage forms, for example, containing 0.01 to 500 mg, and in particular 0.1 mg to 200 mg of active ingredient per unit dosage form.

In some embodiments, the pharmaceutical preparation is in a unit dosage form. In such form, the preparation is subdivided into suitably sized unit doses containing appropriate quantities of the active component, e.g., an effective amount to achieve the desired purpose. The quantity of active compound in a unit dose of preparation may be varied or adjusted from about 0.01 mg to about 1000 mg, from about 0.01 mg to about 750 mg, from about 0.01 mg to about 500 mg, or from about 0.01 mg to about 250 mg, according to the particular application. The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

Medical Use

A composition comprising crystalline Form I of SEQ ID. NO. 1 or an amorphous form prepared according to a method described herein can be used for treating a cardiovascular or cardiorenal disorder that, for example, would respond favorably to a decrease in blood pressure.

In some embodiments, methods of treating cardiovascular disorders are provided. In some embodiments, the method comprises administering to a subject, or a subject in need thereof, a therapeutically effective amount of crystalline Form I and/or pharmaceutically acceptable salt thereof. In some embodiments, the method comprises administering to a subject, or a subject in need thereof, a therapeutically effective amount of an amorphous form of SEQ ID. NO. 1 prepared according to a method described herein and/or pharmaceutically acceptable salt thereof. These cardiovascular disorders include, but are not limited to, chronic hypertension, hypertensive crisis, acute congestive heart failure, angina, acute myocardial infarction, left ventricular failure, cerebrovascular insufficiency, intracranial haemorrhage, heart failure, acute decompensated heart failure, which can also be referred to as acute heart failure, essential hypertension, post-operative hypertension, hypertensive heart disease, hypertensive renal disease, renovascular hypertension, malignant hypertension, post-renal transplant patient stabilization, dilated cardiomyopathy, myocarditis, post-cardiac transplant patient stabilization, disorders associated with post-stent management, neurogenic hypertension, pre-eclampsia, abdominal aortic aneurysm, and any cardiovascular disorder with a hemodynamic component.

In some embodiments, the cardiovascular disorder is an acute cardiovascular disorder. In some embodiments, the acute cardiovascular disorder is acute hypertensive crisis, toxemia of pregnancy, acute myocardial infarction, acute congestive heart failure, acute heart failure, acute ischaemic heart disease, pulmonary hypertension, post-operative hypertension, migraine, retinopathy and post-operative cardiac/valve surgery.

In some embodiments, methods of treating viral infectious disease linked to AT1R are provided. In some embodiments, the methods comprise administering to a subject in need thereof a therapeutically effective amount of crystalline Form I and/or pharmaceutically acceptable salt thereof. In specific embodiments, the composition is administered by intravenous injection.

Combination Therapies

Methods are also provided for treating any cardiovascular or cardiorenal disorder by administering crystalline Form I and/or an amorphous form prepared according to a method described herein, and/or pharmaceutically acceptable salts thereof, in combination with other drugs for the treatment of cardiovascular and/or cardiorenal disorders. These other drugs include diuretics such as furosemide; vasodilators such as nitroglycerin, nitroprusside, brain natriuretic peptide (BNP), or analogues thereof; inotropes such as dobutamine; angiotensin converting enzyme (ACE) inhibitors such as captopril and enalapril; β blockers such as carvedilol and propranolol; angiotensin receptor blockers (ARBs) such as valsartan and candesartan; and/or aldosterone antagonists such as spironolactone.

In the combination therapies, crystalline Form I or the amorphous form is co-administered with one or more drugs for the treatment of cardiovascular and/or cardiorenal disorders to increase efficacy of treatment of cardiovascular and/or cardiorenal disorders and to reduce side effects associated with high doses of these therapeutics.

The combination therapies described above have synergistic and additive therapeutic effects. An improvement in the drug therapeutic regimen can be described as the interaction of two or more agents so that their combined effect reduces the incidence of adverse event (AE) of either or both agents used in co-therapy. This reduction in the incidence of adverse effects can be a result of, e.g., administration of lower dosages of either or both agent used in the co-therapy. For example, if the effect of Drug A alone is 25% and has an adverse event incidence of 45% at labeled dose; and the effect of Drug B alone is 25% and has an adverse event incidence of 30% at labeled dose, but when the two drugs are combined at lower than labeled doses of each, if the overall effect is 35% (an improvement, but not synergistic or additive) and the adverse incidence rate is 20%, there is an improvement in the drug therapeutic regimen.

In some embodiments, the compounds described herein are administered as a mono-therapy. In some embodiments, the compounds described herein are administered as part of a combination therapy. For example, a compound may be used in combination with other drugs or therapies that are used in the treatment/prevention/suppression and/or amelioration of the diseases or conditions for which compounds are useful.

Such other drug(s) may be administered, by a route and in an amount commonly used therefore, contemporaneously or sequentially with the compounds described herein. When a compound described herein is used contemporaneously with one or more other drugs, a pharmaceutical unit dosage form containing such other drugs in addition to the compound described herein may be employed. Accordingly, the pharmaceutical compositions include those that also contain one or more other active ingredients, in addition to the compounds described herein.

A subject or patient in whom administration of the therapeutic compound is an effective therapeutic regimen for a disease or disorder is often a human, but can be any animal, including a laboratory animal in the context of a clinical trial or screening or activity experiment. Thus, as can be readily appreciated by one of ordinary skill in the art, the methods, compound and compositions are particularly suited to administration to any animal, such as a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The following examples are merely illustrative and should not be construed as limiting the scope of the embodiments in any way as many variations and equivalents that are encompassed by these embodiments will become apparent to those skilled in the art upon reading the present disclosure.

EXAMPLES

Example 1A 100 mg SEQ.ID. NO. 1 was gradually dissolved in 0.5 ml of aqueous solution (deionized water). The mixture was vortexed until the sample completely dissolved. The mixture was allowed to sit at ambient condition for precipitation. After a suitable formation period, crystalline Form I was carefully isolated and dried. Form I was then characterized using X-ray powder diffractometry. FIG. 4 shows the X-ray powder diffraction pattern of Form I.

Figure 11:
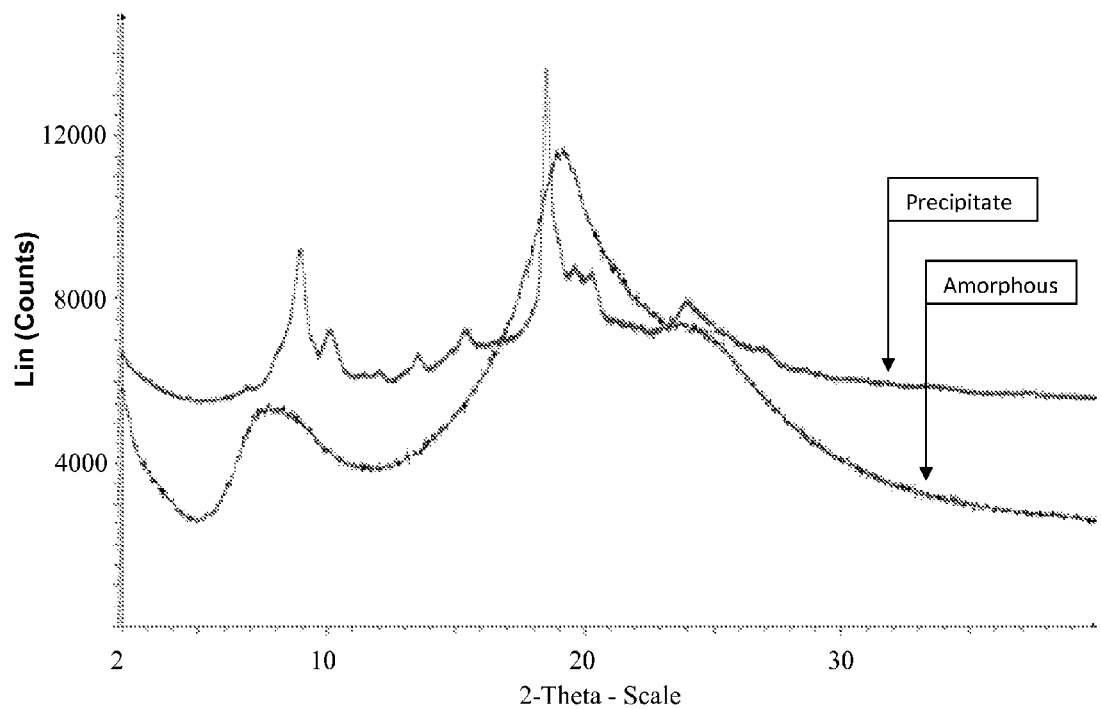
FIG. 11 shows the overlaid X-ray powder diffraction patterns for the precipitate of SEQ.ID. NO. 1 from ethanol and amorphous SEQ.ID. NO. 1.

Example 1B 50 mg SEQ.ID. NO. 1 was gradually dissolved in 0.25 ml of ethanol. The mixture was vortexed until the sample completely dissolved. The mixture was allowed to sit at ambient condition for precipitation. After a suitable formation period of about 12 hours to 48 hours, the precipitate was carefully isolated and dried on an evaporator under continuous flow of nitrogen for about 12 hours to 48 hours. The precipitate was then characterized using X-ray powder diffractometry. FIG. 11 shows the X-ray powder diffraction pattern of the precipitate from ethanol.

Figure 12:
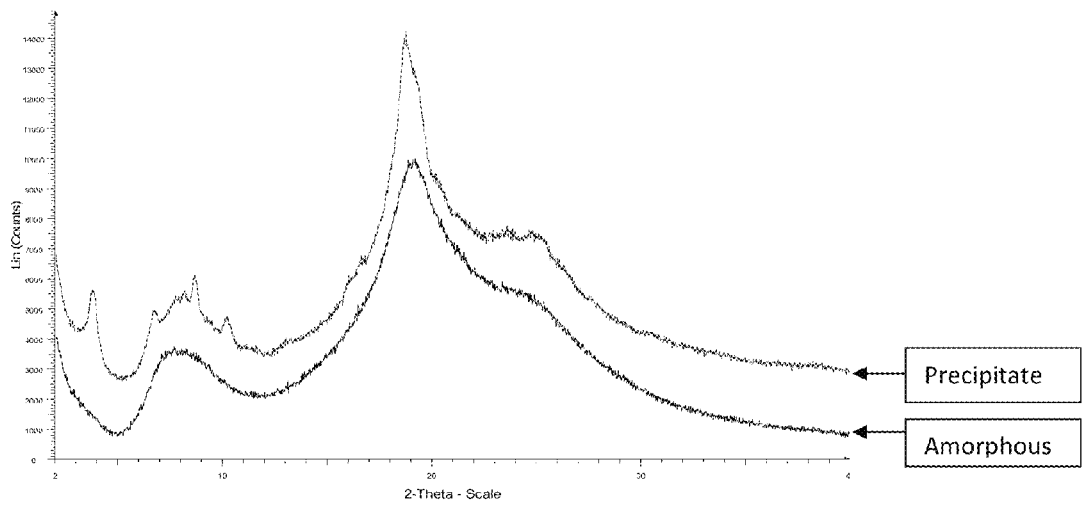
FIG. 12 shows the X-ray powder diffraction pattern for the precipitate of SEQ.ID. NO. 1 from water and acetone.

Example 1C 500 mg SEQ.ID. NO. 1 was gradually dissolved in 2 ml of water and the mixture was warmed to an appropriate temperature in the range of 10° C. to 60° C. To this mixture, acetone was added. The mixture was cooled to ambient temperature and was stirred for about 2-5 hours. The suspension was carefully filtered and isolated, and rinsed with acetone and dried under vacuum. The precipitate was then characterized using X-ray powder diffractometry. FIG. 12 shows the X-ray powder diffraction pattern of the precipitate from water and acetone.

Figure 13:
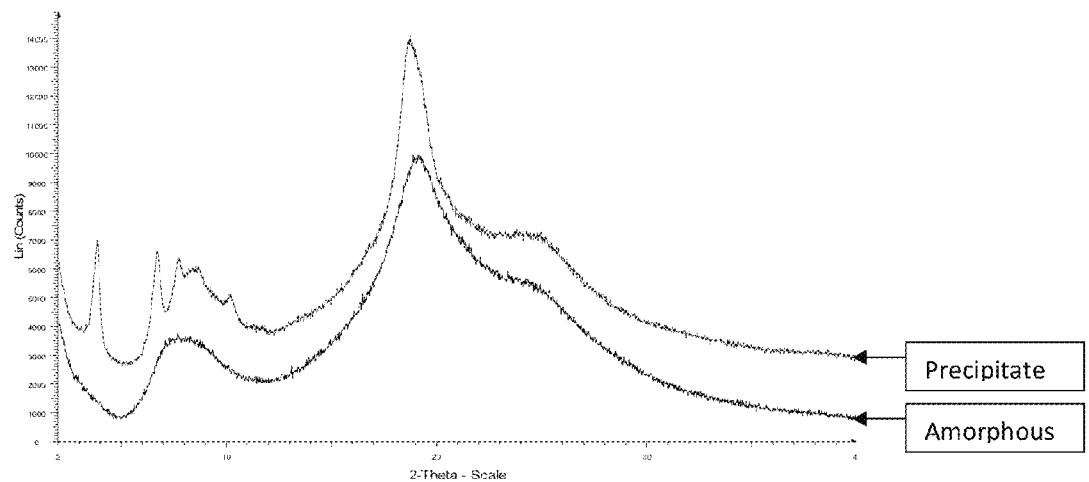
FIG. 13 shows the X-ray powder diffraction pattern for the precipitate of SEQ.ID. NO. 1 from water and isopropyl alcohol.

Example 1D 500 mg SEQ.ID. NO. 1 was gradually dissolved in 2 ml of water and the mixture was warmed to an appropriate temperature in the range of 10° C. to 60° C. To this mixture, 5 ml isopropyl alcohol was added. The mixture was cooled to ambient temperature and was stirred for about 2-5 hours. The suspension was carefully filtered and isolated, and rinsed with isopropyl alcohol and dried under vacuum. The precipitate was then characterized using X-ray powder diffractometry. FIG. 13 shows the X-ray powder diffraction pattern of the precipitate from water and isopropyl alcohol.

Figure 14:
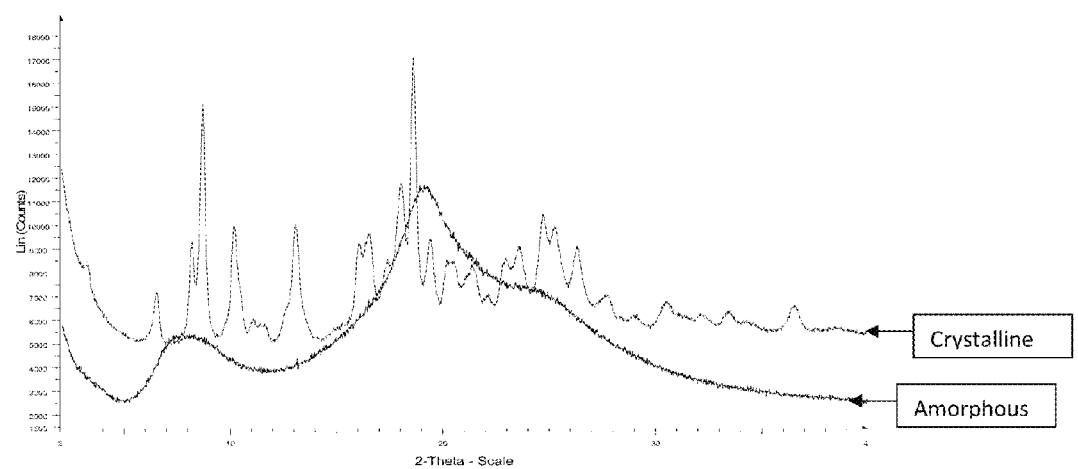
FIG. 14 shows overlaid X-ray powder diffraction patterns for Form I of SEQ.ID. NO. 1 and amorphous SEQ.ID. NO. 1. Corresponding DSC thermogram is shown in FIG. 16.
Figure 16:
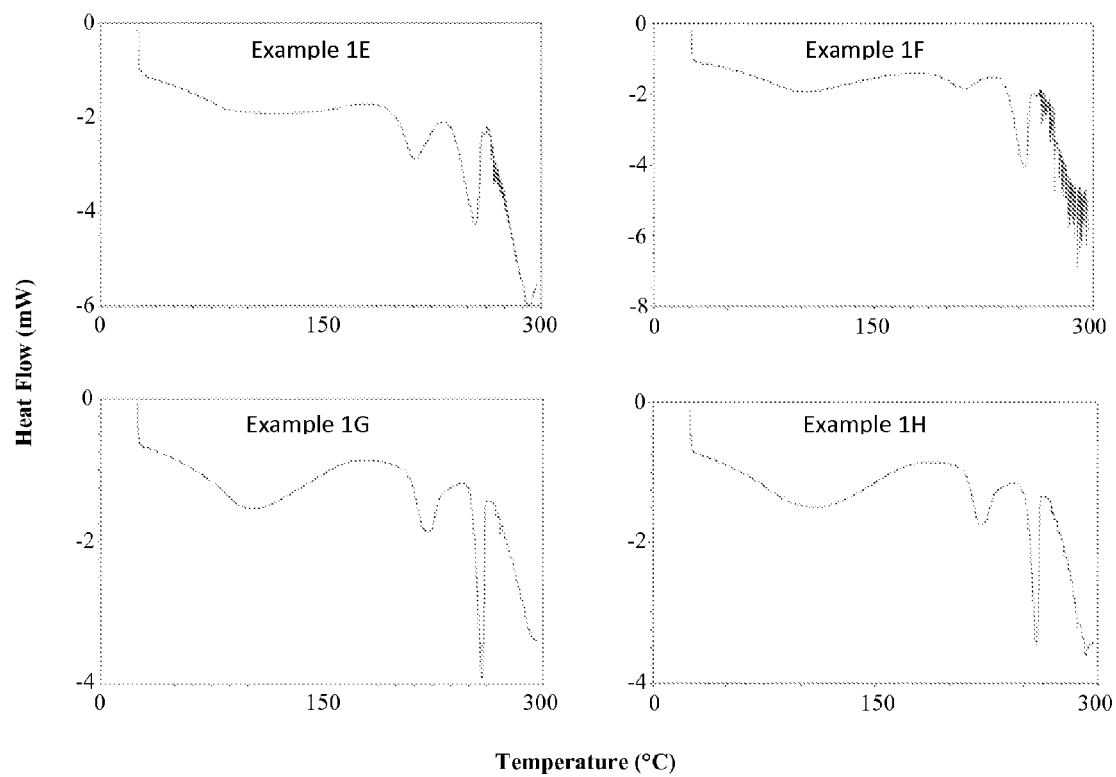
FIG. 16 shows a DSC thermogram for compounds produced according to Examples 1E, 1F, 1G, and 1H.

Example 1E 500 mg SEQ.ID. NO. 1 was gradually dissolved in 1 ml of water at an appropriate temperature in the range of 10° C. to 60° C. The mixture was cooled to ambient temperature and was stirred for about 2-5 hours. The suspension was carefully isolated, and dried. Form I was then characterized using X-ray powder diffractometry. FIG. 14 shows the X-ray powder diffraction pattern of Form I of SEQ.ID. NO. 1. Corresponding DSC thermogram is shown in FIG. 16.

Figure 15:
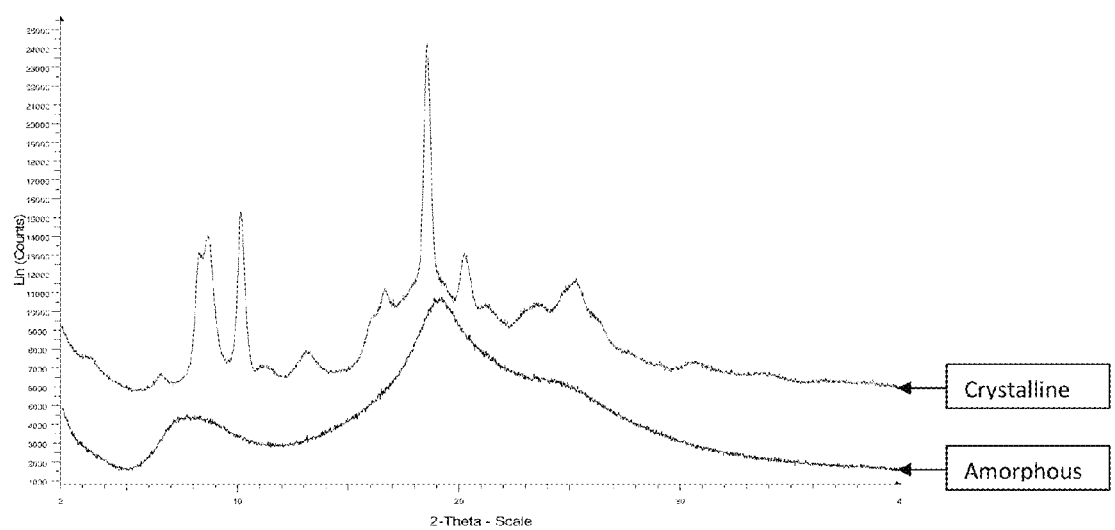
FIG. 15 shows overlaid X-ray powder diffraction pattern for Form I of SEQ.ID. NO. 1 and amorphous SEQ.ID. NO. 1. Corresponding DSC thermogram is shown in FIG. 16.

Example 1F 500 mg SEQ.ID. NO. 1 was gradually dissolved in 1.5 ml of water at an appropriate temperature in the range of 10° C. to 60° C. The mixture was cooled to ambient temperature and was stirred for about 2-5 hours and acetone was added. The suspension was carefully filtered and isolated, and dried. Form I was then characterized using X-ray powder diffractometry. FIG. 15 shows the X-ray powder diffraction pattern of Form I. Corresponding DSC thermogram is shown in FIG. 16.

Figure 17:
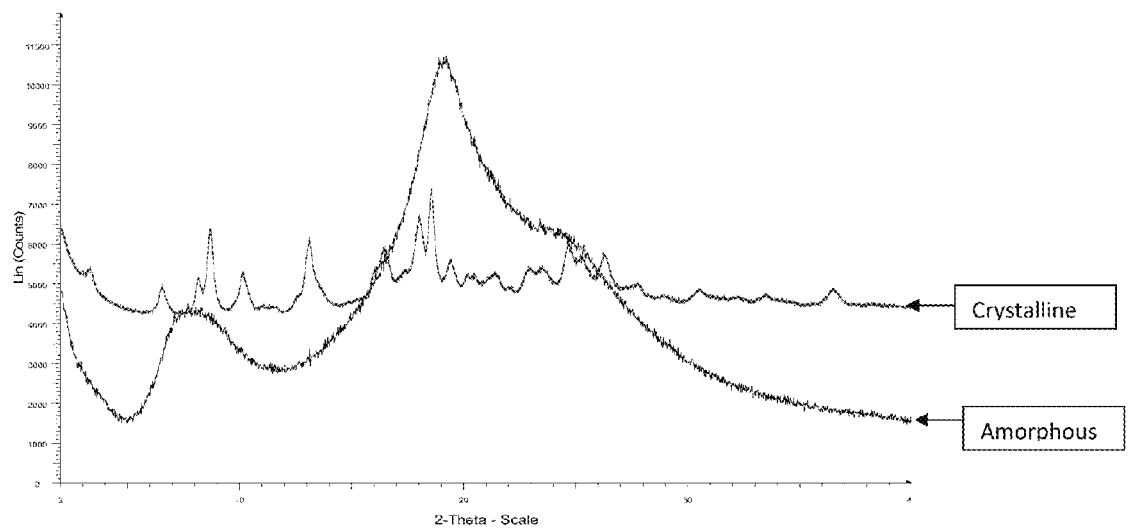
FIG. 17 shows overlaid X-ray powder diffraction pattern for Form I of SEQ.ID. NO. 1 and amorphous SEQ.ID. NO. 1. Corresponding DSC thermogram is shown in FIG. 16.

Example 1G 500 mg SEQ.ID. NO. 1 was gradually dissolved in 2.5 ml of water at an appropriate temperature in the range of 10° C. to 60° C. The mixture was cooled to ambient temperature. The suspension was carefully isolated, and dried under vacuum. Form I was then characterized using X-ray powder diffractometry. FIG. 17 shows the X-ray powder diffraction pattern of Form I. Corresponding DSC thermogram is shown in FIG. 16.

Figure 18:
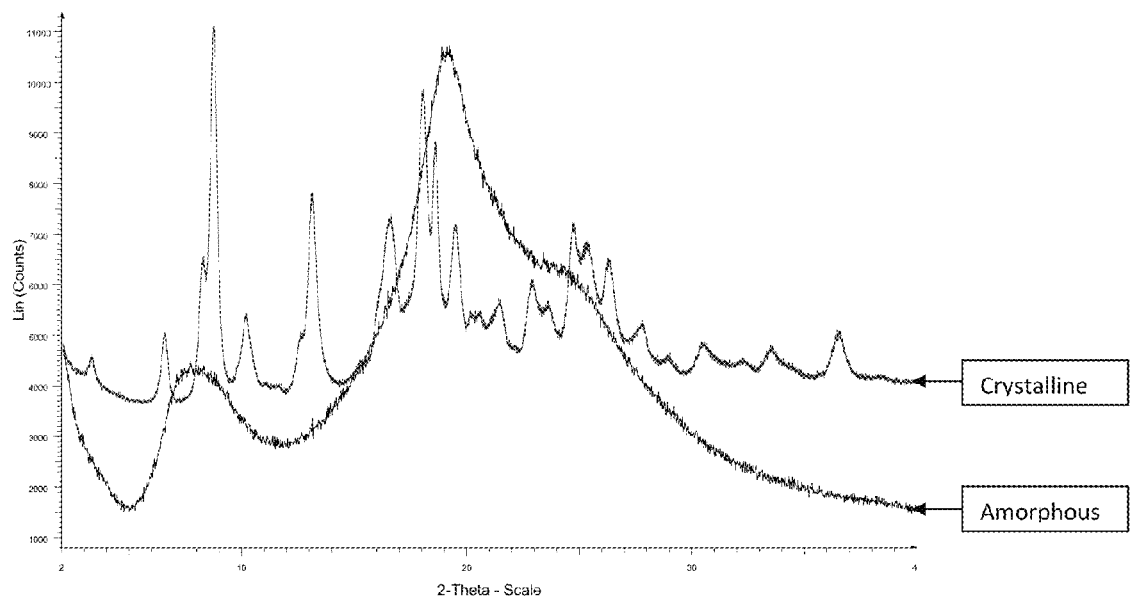
FIG. 18 shows overlaid X-ray powder diffraction pattern for Form I of SEQ.ID. NO. 1 and amorphous SEQ.ID. NO. 1. Corresponding DSC thermogram is shown in FIG. 16.

Example 1H 500 mg SEQ.ID. NO. 1 was gradually dissolved in 3.5 ml of water at an appropriate temperature in the range of 10° C. to 60° C. The mixture was cooled to ambient temperature. The suspension was stirred at room temperature and was carefully isolated by filtration, and dried under vacuum. Form I was then characterized using X-ray powder diffractometry. FIG. 18 shows the X-ray powder diffraction pattern of Form I. Corresponding DSC thermogram is shown in FIG. 16.

The chemical identity of crystalline Form I was determined using High Pressure Liquid Chromatography (HPLC) and Waters Sunfire C18 column (5 μm, 4.6×250 mm, Part #186002560) with UV detection at 215 nm. The column temperature was set at about 30-65° C. A gradient method consisting of 0.1% trifluoroacetic acid in deionized water as mobile phase A and 0.1% trifluoroacetic in methanol/DI water mixture (2:1 v/v) as mobile phase B was used at a flow rate of 1.0 mL/min with a run time of 39 min for each sample. Samples of amorphous SEQ.ID. NO. 1 and crystalline Form I were prepared in DI water at the same concentration of around 1.2 mg/mL and injected at a volume of 20 μL. Data was acquired and analyzed by TotalChrom® Chromatography Data System software (Perkin Elmer, Inc., Waltham, Mass.). Solubility of SEQ.ID.NO.1 in solvents as described above was unexpected and surprising and it allowed for successful precipitation and isolation of SEQ.ID.NO.1, which is necessary for large scale manufacturing for commercial production.

XRD characterization of Form I from supersaturated aqueous solution indicated that it is crystalline material. DSC thermogram of Form I also showed different endothermic transitions from amorphous SEQ.ID. NO. 1, with the last endothermic peak appeared to be around 255° C.-259° C. The HPLC chromatograms confirmed that the crystalline form prepared from supersaturated aqueous solution is chemical the same as SEQ.ID. NO. 1 amorphous form.

These results suggest that Form I from water is a crystalline form of SEQ.ID. NO. 1. Results also suggest that the precipitates from ethanol, acetone/water and isopropyl alcohol/water showed same XRD pattern (FIGS. 11-13) as the amorphous SEQ.ID. NO. 1 and that they may comprise amorphous, mostly amorphous, a mixture of amorphous and crystalline forms, one or more crystalline forms, or a mixture of amorphous and one or more crystalline forms.

Example 2

XRPD Analysis

The X-ray powder diffraction patterns of Example 1 were determined using a bench-top X-ray diffractometer D8 Advance, Bruker AXS Inc., Madison, Wis.). A small amount of sample obtained from Example 1 was loaded onto Si-low background sample holder, and exposed to CuKα radiation (40 kV×40 mA). The sample was scanned in a locked coupled mode with spinner rotating at a speed of 25 rpm. The angular range was 2° to 40° 2θ in a step size of 0.0069, number of steps of 5470 and timestep of 0.39 second. Data collection and analyses were performed with commercially available software (Eva, version 2.0, Bruker AXS Inc., Madison, Wis.).

FIG. 4 shows the X-ray powder diffraction pattern for crystalline Form I. Peak positions are provided in Table 1.

TABLE 1

| Angle (2θ) | d value (Angstrom) |
|---|---|
| 6.182 | 14.28439 |
| 8.242 | 10.71841 |
| 8.633 | 10.2345 |
| 10.103 | 8.74851 |
| 10.71 | 8.24109 |
| 11.451 | 7.72162 |
| 12.364 | 7.15297 |
| 13.248 | 6.67774 |

TABLE 1-continued

| Angle (2θ) | d value (Angstrom) |
|---|---|
| 14.081 | 6.28461 |
| 15.452 | 5.72976 |
| 16.103 | 5.49955 |
| 16.58 | 5.34234 |
| 17.323 | 5.11512 |
| 17.825 | 4.97193 |
| 18.516 | 4.78809 |
| 19.197 | 4.6198 |
| 20.14 | 4.37666 |
| 20.902 | 4.24645 |
| 21.517 | 4.12648 |
| 23.149 | 3.83918 |
| 24.423 | 3.64173 |
| 26.247 | 3.39266 |
| 1.812 | 3.20517 |
| 30.801 | 2.9006 |
| 32.472 | 2.75505 |
| 33.577 | 2.66691 |
| 38.428 | 2.34063 |

Example 3

Differential Scanning Calorimetry Analysis

Crystalline Form I was analyzed using Differential Scanning Calorimetry. A differential scanning calorimeter (DSC Q2000, TA Instruments, New Castle, Del.) with a refrigerated cooling accessory was used for the analysis. Approximately 2 to 5 mg of sample obtained from Example 1 was weighed and heated under dry nitrogen purge (flow rate of 50 mL/min) from 25° C. to 300° C. at 10° C./min. Data was analyzed using Universal Analysis (TA Instruments, New Castle, Del.) 1.1.3 Dynamic Vapor Sorption (DVS)

The moisture sorption-desorption profiles of amorphous SEQ.ID. NO. 1 were obtained using a DVS Intrinsic Vapor Sorption Analyzer (Surface Measurement Systems Ltd, Allentown, Pa.) and are shown in FIG. 3. A small quantity of sample from Example 1 was placed in a DVS sample holder. Two cycles of sorption desorption profile were recorded at 25° C. in the range of 0% to 95% RH (the first sorption cycle was started at 45% RH) with maximum equilibration time of 120 min at each step (0%, 5%, 15%, 25%, 35%, 45%, 55%, 65%, 75%, 85%, 95%).

Example 4

Microscopic Analysis

A polarized light microscope (Nikon Eclipse E600 POL, Morrell Instrument Company, Melville, N.Y.) with Plan Fluor 10× objective was used. A tiny amount of sample was placed onto glass slide by spatula. The sample was then placed on circular rotating stage of the microscope. Sample was first observed under plane polarized light and then observed cross polarized light for birefringence phenomena. Images were captured and particle size was analyzed by Image-Pro® Plus version 5.0 (Media Cyberneics, Inc., Rockville, Md.). Form I from water was further examined using polarized microscopy. Results confirmed that the sample was crystalline material as birefringence was observed in the sample under cross polarized light after turning the sample stage from 0° to 90° angle as shown in FIG. 9. Particle size was also determined as shown in FIG. 10 and Table 2.

TABLE 2

| Obj.# | Area | Size (length) μm | Size (width) μm |
|---|---|---|---|
| 1 | 297 | 24.4 | 17.6 |
| 2 | 2383 | 95.4 | 47.2 |
| 4 | 638 | 35.2 | 25.2 |
| 5 | 992 | 50.3 | 34.2 |
| 6 | 2635 | 96.7 | 39.4 |
| 7 | 3467 | 93.5 | 61.9 |
| 9 | 475 | 44.8 | 14.6 |
| 10 | 2123 | 87.7 | 40.8 |

XRD characterization of Form I from supersaturated aqueous solution indicated that it is crystalline material. DSC thermogram of Form I also showed different endothermic transitions from amorphous SEQ.ID. NO. 1, with the last endothermic peak appeared to be around 255° C.-259° C. The HPLC chromatograms confirmed that the crystalline form prepared from supersaturated aqueous solution is chemical the same as SEQ.ID. NO. 1 amorphous form. These results suggest that Form I from water is a crystalline form of SEQ.ID. NO. 1. By contrast, the precipitate from ethanol showed same XRD pattern as the amorphous SEQ.ID. NO. 1 indicating that at least some amorphous material may be present in the precipitate.

Example 5

Form I has Surprising and Unexpected Properties

Methods

Appearance: The appearance and flow property of crystalline powder was examined visually and photographic image was taken using a Nikon D3100 Digital SLR (14.2 MP with 18-55 mm f/3.5-5.6 AF-S DX VR Nikkor Zoom Lens) digital camera.

Bulk Density: The bulk density of amorphous and crystalline form is roughly determined by dividing the weight of powder in gram by the volume of the weighted amount in mL. The powder is accurately weighed on a calibrated balance; the volume is measured by transferring the weighed amount in a graduated cylinder.

Thermogravimetry Analysis (TGA): A thermogravimetric analyzer (TGA Q5000IR, TA Instruments, New Castle, Del.) with air cooling was used. About 2 mg of sample was weighed in platinum TGA pan and heated under dry nitrogen purge (flow rate 25 ml/min) at 10° C./min. The data was analyzed using Universal Analysis (TA instruments, New Castle, Del.).

Dynamic Vapor Sorption (DVS): The moisture sorption-desorption profile of Form I was obtained using a DVS Intrinsic Vapor Sorption Analyzer (Surface Measurement Systems Ltd, Allentown, Pa.). A small quantity of sample was placed in a DVS sample holder. 2 cycles of sorption desorption profile were recorded at 25° C. in the range of 0% to 95% RH (the first sorption cycle was started at 45% RH) with maximum equilibration time of 120 min at each step (0%, 5%, 15%, 25%, 35%, 45%, 55%, 65%, 75%, 85%, 95%).

Stability Study: The effects of temperature and humidity on amorphous and crystalline (Form I) SEQ.ID.NO.1 was evaluated, this is to provide assessment on the solid state stability of the crystalline SEQ.ID.NO.1. Approximately 1.6 mg of SEQ.ID.NO.1 was kept in an open scintillation vial in various temperatures and relative humidity conditions. The study design is provided in Table 3

TABLE 3

Stability Study Design

| Storage Temperature | Relative Humidity | Time points |
|---|---|---|
| 25° C. | 60% | 2, 4, 8, and 12 weeks |
| 40° C. | 11%, 32%, 75%, 90% | 2, 4, 8, and 12 weeks |
| 50° C. | 75% | 2, 4, 8, and 12 weeks |

Powder X-Ray Diffractometry (PXRD): A small amount of sample was loaded onto Si-low background sample holder, and exposed to CuKα radiation (40 kV×40 mA) in an X-ray diffractometer (D8 Advance, Bruker AXS Inc., Madison, Wis.). The sample was scanned in a locked coupled mode with spinner rotating at a speed of 25 rpm. The angular range was 2° to 40° 2θ in a step size of 0.0069, number of steps of 5470 and timestep of 0.39 second. The data collection and analyses were performed with commercially available software (Eva, version 2.0, Bruker AXS Inc., Madison, Wis.).

Determination of Degradation Product: The amount of degradation products in the composition comprising SEQ.ID.NO.1 was quantified by UPLC with UV detection at 205 nm using procedure described in method PRD-TM-ANL-01105 version 1.0.

Results

Appearance: The color of crystalline form SEQ.ID.NO.1 (Form I) remained the same as the amorphous form. In addition, it was found that the crystalline form had better flow property as compared to the amorphous form.

Bulk Density: The bulk density of amorphous and crystalline SEQ.ID.NO.1 was determined to be 0.07 g/ml and 0.4 g/ml, respectively. Thus, the bulk density of crystalline SEQ.ID.NO.1 was improved significantly and is approximately 6-fold higher than the amorphous material. This significant increase in bulk density of the crystalline form could not have been predicted.

Figure 19:
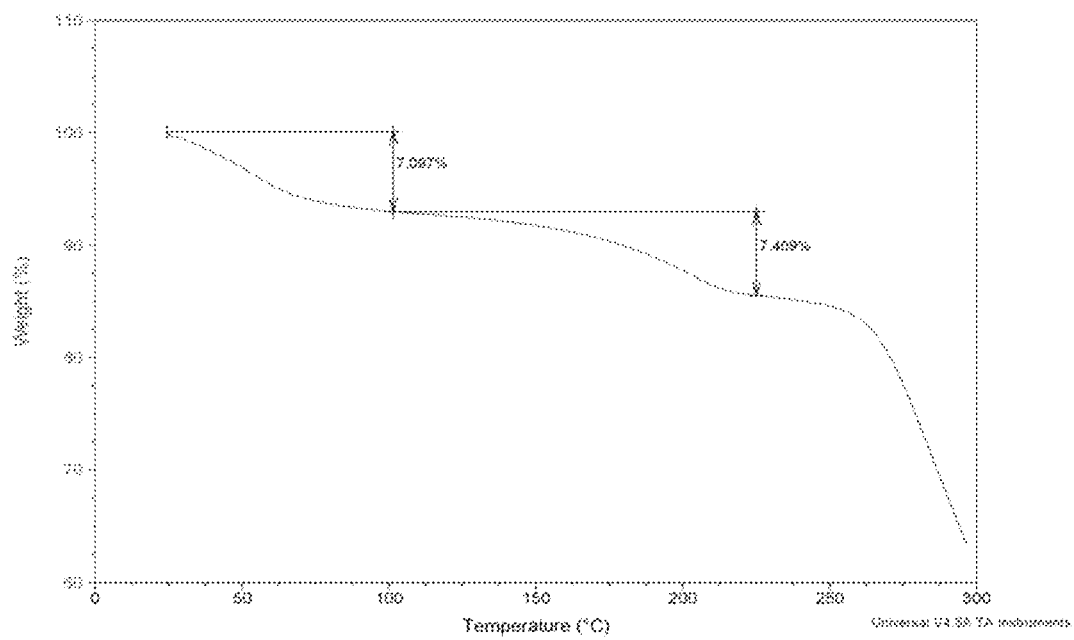
FIG. 19 shows a TGA profile of crystalline SEQ.ID.NO.1.

TGA: The TGA weight loss curve of crystalline SEQ.ID.NO.1 presented in FIG. 19 exhibits two weight-loss steps. The first weight loss event of 7.1% w/w occurs between 25° C. to 100° C.; the second one of 7.4% w/w occurs between 100° C. to 225° C. The two weight loss events matches the broad endotherms observed from the DSC thermogram and are associated with the loss of water and residual acetic acid present in the material. The data is shown in FIG. 19.

Figure 20:
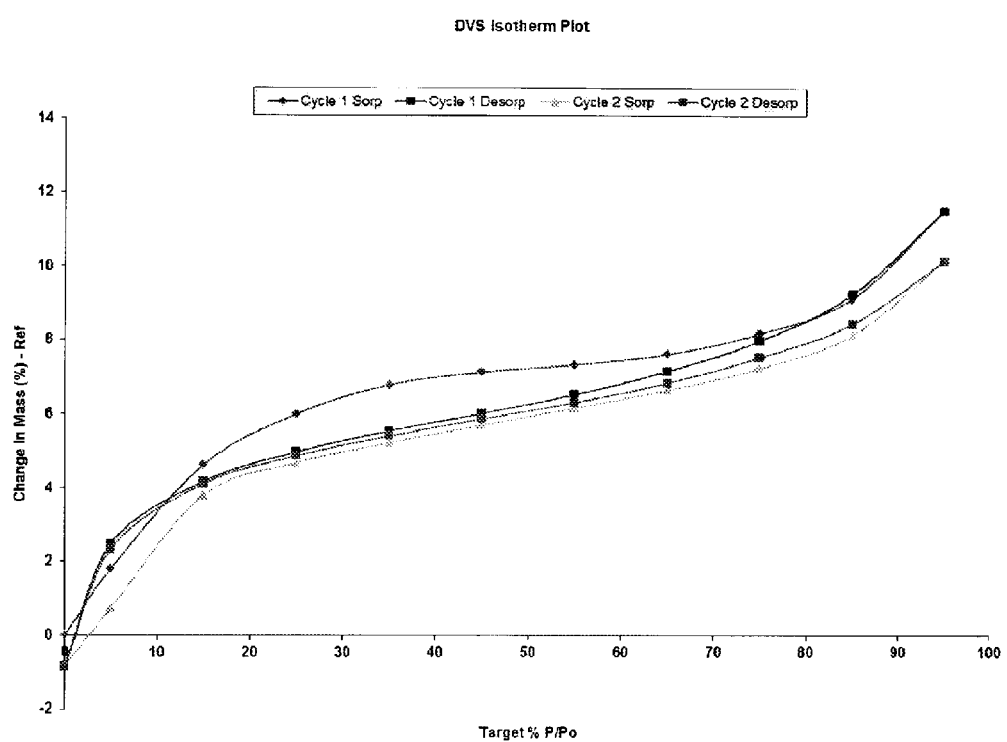
FIG. 20 shows FIG. 20 a DVS profile of crystalline SEQ.ID.NO.1.
Figure 21:
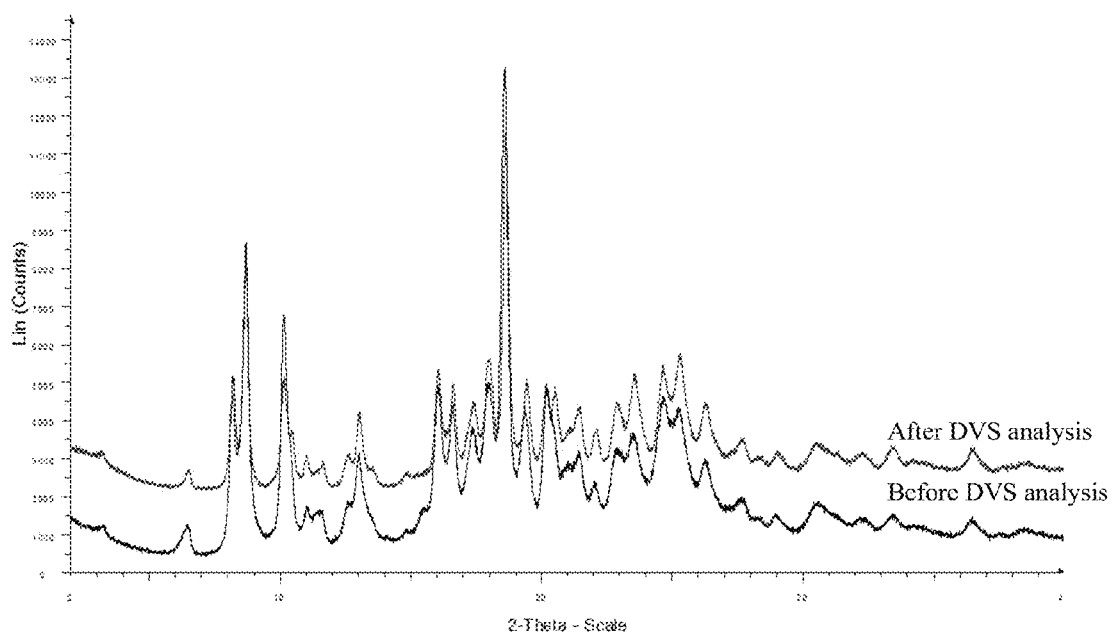
FIG. 21 shows the PXRD of crystalline form SEQ.ID.NO.1 after completion of DVS analysis.

Dynamic Vapor Sorption (DVS): The DVS data (FIG. 20) shows that crystalline SEQ.ID.NO.1 is not as hygroscopic as amorphous SEQ.ID.NO.1. The crystalline form only adsorbed roughly 7.6% (by weight) at 60% RH and 11% (by weight) at 95% RH. However, amorphous form adsorbed more than 10% (by weight) at 60% RH and 30% (by weight) at 95% RH. After completion of DVS analysis, the sample was characterized by X-ray powder diffractometry. FIG. 21 shows that the crystalline form remained unchanged after exposing to two sorption/desorption cycles.

Figure 22:
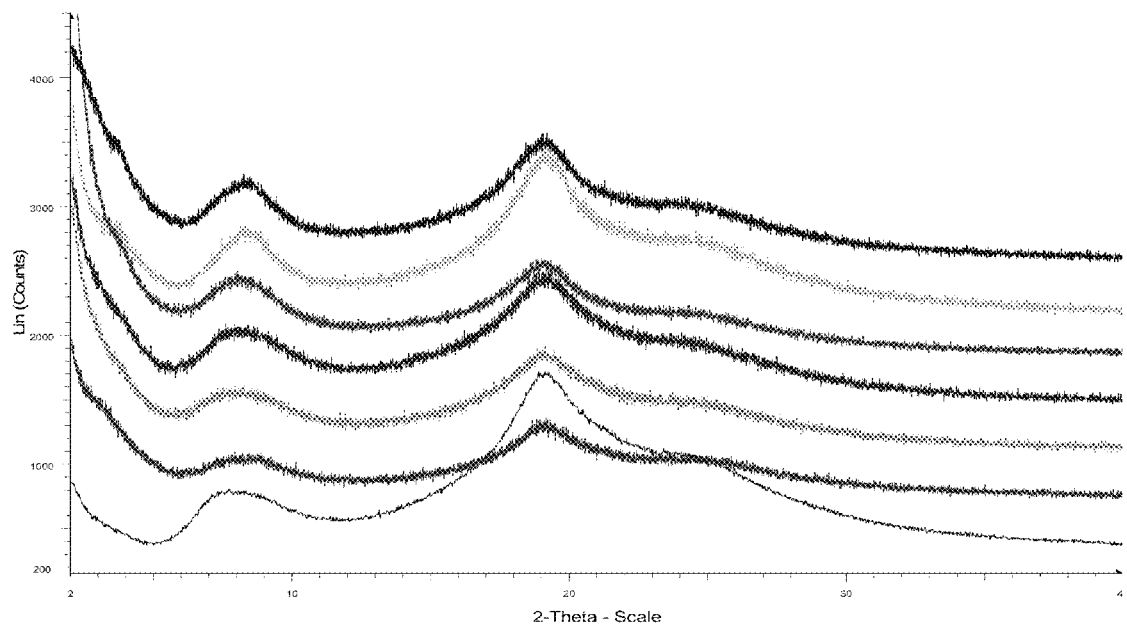
FIG. 22 shows PXRD patterns of amorphous SEQ.ID.NO.1 at various temperature and humidity conditions.
Figure 23:
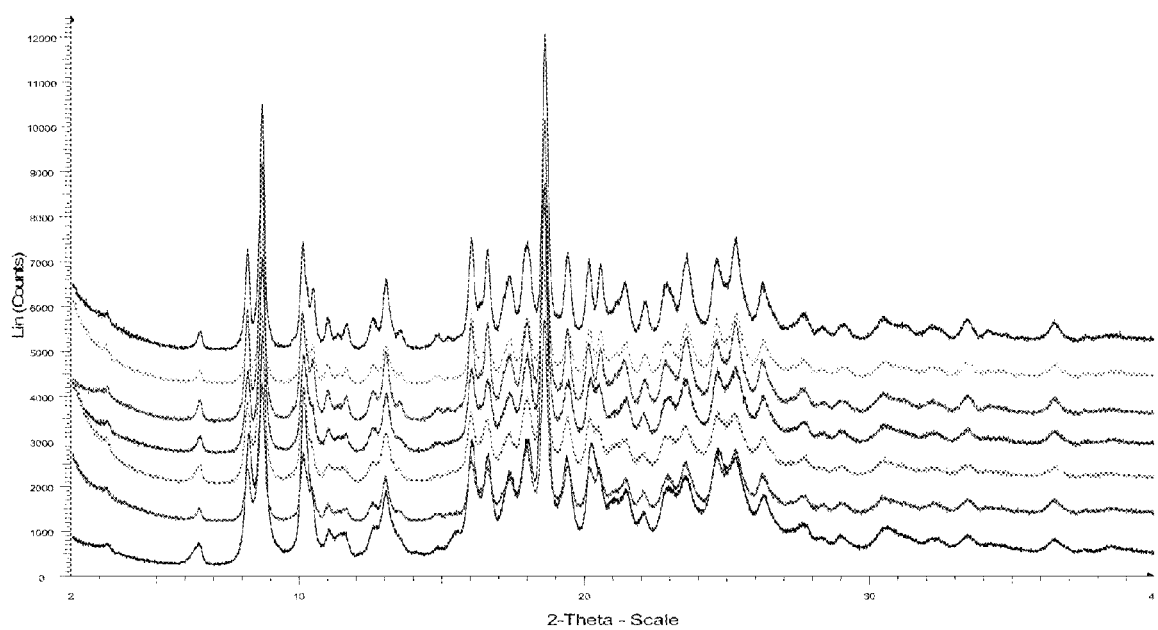
FIG. 23 shows PXRD patterns of crystalline SEQ.ID.NO.1 at various temperature and humidity conditions.

Stability Study: The PXRD patterns of amorphous and crystalline SEQ.ID.NO.1 after 3 months of storage at various conditions are displayed in FIG. 22 and FIG. 23, respectively. The solid state form of both materials remains stable at all time-points and various temperature/humidity conditions. The results of total degradation of amorphous and crystalline SEQ.ID.NO.1 are provided in Table 4. The total degradation of amorphous SEQ.ID.NO.1 increase significantly as a function of time at high temperature and humidity conditions. At elevated conditions of 40° C./75% RH, 40° C./90% RH and 50° C./75% RH, a high level of hydrolytic degradation product is detected, which is the main contributor to the total degradation products of amorphous SEQ.ID.NO.1. The degradation products of crystalline SEQ.ID.NO.1 did not increase as significantly as compared to the amorphous form. There was only approximately 0.4% total degradation increased for crystalline SEQ.ID.NO.1 at 25° C./60% RH, 40° C./11% RH and 40° C./32% RH. At elevated conditions of 40° C./75% RH, 40° C./90% RH and 50° C./75% RH, hydrolytic degradation product is also the main contributor to the total degradation products, however, the level observed in crystalline SEQ.ID.NO.1 is significantly lower than the one determined in amorphous SEQ.ID.NO.1. Accordingly, crystalline SEQ.ID.NO.1 is significantly, and unexpectedly, chemically more stable than amorphous SEQ.ID.NO.1.

TABLE 4

Total degradation results of amorphous and crystalline SEQ.ID.NO.1 at various stability conditions

| | Initial | 2 wk | 4 wk | 8 wk | 12 wk |
|---|---|---|---|---|---|
| Amorphous SEQ.ID.NO.1 | | | | | |
| 25° C./60% RH | 0.75% | 1.08% | 1.60% | 1.40% | 1.86% |
| 40° C./11% RH | | 1.17% | 1.50% | 1.44% | 2.07% |
| 40° C./32% RH | | 0.91% | 1.73% | 1.45% | 1.65% |
| 40° C./75% RH | | 1.39% | 2.30% | 3.79% | 4.06% |
| 40° C./90% RH | | 3.36% | 6.04% | 9.93% | 13.18% |
| 50° C./75% RH | | 2.10% | 3.22% | 34.75% | 38.15% |
| Crystalline SEQ.ID.NO.1 | | | | | |
| 25° C./60% RH | 0.65% | 0.73% | 0.90% | 1.05% | 1.00% |
| 40° C./11% RH | | 0.72% | 1.21% | 0.89% | 1.04% |
| 40° C./32% RH | | 0.74% | 1.01% | 0.95% | 1.08% |
| 40° C./75% RH | | 0.85% | 1.16% | 1.09% | 1.44% |
| 40° C./90% RH | | 1.03% | 1.34% | 1.68% | 1.50% |
| 50° C./75% RH | | 0.80% | 1.47% | 4.52% | 4.64% |

As is demonstrated in the Examples, and as is discussed in this application, the crystalline Form I has physical properties that are surprising and unexpected as compared to amorphous form. For example, the data demonstrates that crystalline Form I has enhanced bulk density properties as compared to the amorphous form, which enables the product to have better handling, easier storage (does not take up as much space), and better flow in manufacturing. The crystalline form also has better chemical stability as compared to the amorphous form, and it is less hygroscopic. Thus, because of these two improved stability factors, Form I is unexpectedly and surprisingly more stable and, unexpectedly, can be stored at either controlled refrigerated temperature (4 C) or at room temperature (20-25 C), which is a significant and unexpected advantage over the amorphous form, which is stored at −20 C. The ability to store Form I at a higher temperature is unexpected, in part, because it is unusual for a crystalline form of a peptide to have this increase in stability at the higher temperatures (>−20 C) especially in view of the hygroscopic properties of the amorphous form of SEQ.ID.NO.1, The crystalline Form I of SEQ.ID. NO. 1 is also expected to have synergy with other active or inactive components resulting in enhanced performance characteristics or properties of pharmaceutical compositions comprising one or more crystalline forms of the compounds described herein.

EQUIVALENTS

While the embodiments have been depicted and described by reference to exemplary embodiments, such a reference does not imply a limitation on the scope, and no such limitation is to be inferred. The embodiments are capable of considerable modification, alteration, and equivalents in form and function, as will occur to those ordinarily skilled in the pertinent arts having the benefit of this disclosure.

The depicted and described embodiments are exemplary only, and are not exhaustive of the scope.

All references cited herein are hereby incorporated by reference in their entirety.

What is claimed is:

1. A crystalline form of a polypeptide having the amino acid sequence SEQ.ID.NO.1, wherein the form is Form I of SEQ.ID.NO.1.

2. The crystalline Form I of claim 1 characterized by an X-ray powder diffraction pattern comprising a peak at about 18.5±0.5 degrees 2θ.

3. The crystalline Form I of claim 1 characterized by an X-ray powder diffraction pattern comprising peaks at about 18.5±0.5 degrees 2θ and at about 10.1±0.5 degrees 2θ.

4. The crystalline Form I of claim 1 characterized by an X-ray powder diffraction pattern comprising peaks:
at about 20.2±0.5 degrees 2θ, at about 10.1±0.5 degrees 2θ, and at about 24.4±0.5 degrees 2θ.

5. The crystalline Form I of claim 1 characterized by an X-ray powder diffraction pattern comprising one or more peaks at about 18.5±0.5 degrees 2θ, at about 10.1±0.5 degrees 2θ, at about 8.2±0.5 degrees 2θ, at about 20.2±0.5 degrees 2θ, and at about 24.4±0.5 degrees 2θ.

6. The crystalline Form I of claim 1 characterized by an X-ray powder diffraction pattern comprising one or more peaks as shown in FIG. 4.

7. The crystalline Form I of claim 1 characterized by an X-ray powder diffraction pattern comprising one or more d-spacing values at about 10.7±0.5 degrees angstroms, at about 8.7±0.5 degrees angstroms, at about 4.7±0.5 degrees angstroms, at about 4.1±0.5 degrees angstroms, and at about 3.6±0.5 degrees angstroms.

8. A pharmaceutical composition comprising the crystalline Form I of claim 1.

9. The pharmaceutical composition of claim 8, further comprising an additional drug for the treatment of a cardiovascular or a cardiorenal disorder.

10. The crystalline Form I of claim 1 characterized by an X-ray powder diffraction pattern comprising a peak at about 10.1±0.5 degrees 2θ.

11. The crystalline Form I of claim 1 characterized by an X-ray powder diffraction pattern comprising a peak at about 8.2±0.5 degrees 2θ.

12. The crystalline Form I of claim 1 characterized by an X-ray powder diffraction pattern comprising a peak at about 20.2±0.5 degrees 2θ.

13. The crystalline Form I of claim 1 characterized by an X-ray powder diffraction pattern comprising a peak at about 24.4±0.5 degrees 2θ.

14. The crystalline Form I of claim 1 characterized by an X-ray powder diffraction pattern comprising peaks at about 10.1±0.5±0.5 degrees 2θ and at about 8.2±0.5 degrees 2θ.

15. The crystalline Form I of claim 1 characterized by an X-ray powder diffraction pattern comprising peaks at about 8.2±0.5 degrees 2θ and at about 20.2±0.5 degrees 2θ.

16. The crystalline Form I of claim 1 characterized by an X-ray powder diffraction pattern comprising peaks at about 20.2±0.5 degrees 2θ and at about 10.1±0.5 degrees 2θ.

17. The crystalline Form I of claim 1 characterized by an X-ray powder diffraction pattern comprising peaks at about 20.2±0.5 degrees 2θ and at about 24.4±0.5 degrees 2θ.

18. The crystalline Form I of claim 1 characterized by an X-ray powder diffraction pattern comprising peaks at about 8.2±0.5 degrees 2θ, at about 18.5±0.5 degrees 2θ, and at about 20.2±0.5 degrees 2θ.

19. A process for preparing a crystalline form of a polypeptide having an amino acid sequence of SEQ.ID.NO.1, comprising crystallizing SEQ.ID.NO.1 to form Form I of SEQ.ID.NO.1 and optionally isolating the Form I of SEQ.ID.NO.1.

20. The process of claim 18, wherein the crystallizing comprises dissolving a polypeptide having an amino acid sequence of SEQ.ID. NO.1 in an aqueous solution and crystallizing SEQ.ID.NO.1 to form Form I therefrom.

21. The process of claim 20, wherein the aqueous solution is deionized water.

22. The process of claim 19, wherein the aqueous solution consists of deionized water.

23. A method of treating a cardiovascular or a cardiorenal disorder comprising administering to a patient in need thereof a crystalline Form I of a polypeptide having an amino acid sequence of SEQ.ID.NO.1.

24. The method of claim 23, wherein the cardiovascular or the cardiorenal disorder is heart failure.

25. The method of claim 23, wherein the patient has been diagnosed with heart failure.

* * * * *